United States Patent
Scher et al.

(10) Patent No.: US 9,169,308 B2
(45) Date of Patent: Oct. 27, 2015

(54) METHODS AND COMPOSITIONS OF HUMAN RECOMBINANT GROWTH AND DIFFERENTIATION FACTOR-5 (RHGDF-5) ISOLATED FROM INCLUSION BODIES

(71) Applicant: Warsaw Orthopedic, Inc., Warsaw, IN (US)

(72) Inventors: David S. Scher, Collierville, TN (US); Roger E. Harrington, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/750,793

(22) Filed: Jan. 25, 2013

(65) Prior Publication Data
US 2014/0212952 A1    Jul. 31, 2014

(51) Int. Cl.
| | |
|---|---|
| C12N 1/21 | (2006.01) |
| C12N 15/11 | (2006.01) |
| C12N 15/12 | (2006.01) |
| C12N 15/63 | (2006.01) |
| C12N 15/71 | (2006.01) |
| C12N 15/70 | (2006.01) |
| C07K 14/475 | (2006.01) |

(52) U.S. Cl.
CPC .................................. C07K 14/475 (2013.01)

(58) Field of Classification Search
None
See application file for complete search history.

(56) References Cited

U.S. PATENT DOCUMENTS

| | | | |
|---|---|---|---|
| 2003/0185792 A1* | 10/2003 | Keck et al. | 424/85.1 |
| 2003/0219774 A1* | 11/2003 | Sharma et al. | 435/6 |
| 2009/0298761 A1 | 12/2009 | Engelman et al. | |
| 2009/0318343 A1 | 12/2009 | Garigapati et al. | |
| 2010/0009911 A1 | 1/2010 | Soula | |
| 2010/0015230 A1 | 1/2010 | Ron | |
| 2010/0047299 A1 | 2/2010 | Pohl | |
| 2010/0074936 A9 | 3/2010 | Vukicevic et al. | |
| 2010/0074959 A1 | 3/2010 | Hansom et al. | |
| 2010/0075896 A9 | 3/2010 | Vukicevic et al. | |
| 2010/0105621 A1 | 4/2010 | Cohen et al. | |
| 2010/0112069 A1 | 5/2010 | Beals et al. | |
| 2010/0129342 A1 | 5/2010 | Pohl et al. | |
| 2010/0129415 A1 | 5/2010 | Kinnane et al. | |
| 2010/0130730 A1 | 5/2010 | Garigapati et al. | |
| 2010/0144631 A1 | 6/2010 | Ron | |
| 2010/0166867 A1 | 7/2010 | Soula et al. | |
| 2010/0184659 A1 | 7/2010 | Jaworowicz | |
| 2010/0189757 A1 | 7/2010 | McKay | |
| 2010/0209926 A1 | 8/2010 | Alaoui et al. | |
| 2010/0215731 A1 | 8/2010 | Emans et al. | |
| 2010/0255115 A1 | 10/2010 | Mohan et al. | |
| 2010/0256643 A1 | 10/2010 | McKay | |
| 2010/0266689 A1 | 10/2010 | Simonton et al. | |
| 2010/0286067 A1 | 11/2010 | DeFrees | |
| 2010/0291170 A1 | 11/2010 | Sampath et al. | |
| 2010/0330260 A1 | 12/2010 | McKay | |
| 2011/0020658 A1 | 1/2011 | Hellerbrand et al. | |
| 2011/0021427 A1 | 1/2011 | Amsden et al. | |

(Continued)

Primary Examiner — Elizabeth C Kemmerer
(74) Attorney, Agent, or Firm — Sorell Lenna & Schmidt LLP

(57) ABSTRACT

Expression vector systems are provided for increased production of a recombinant GDF-5 (rhGDF-5) protein. Also provided are transformed host cells that were engineered to produce and express high levels of rhGDF-5 protein. Methods for isolating recombinant GDF-5 protein from an inclusion body of a cell are disclosed herein. The methods as disclosed are cost-effective, time-saving and are of manufacturing quality.

17 Claims, 24 Drawing Sheets

(56) References Cited

U.S. PATENT DOCUMENTS

| | | |
|---|---|---|
| 2011/0027363 A1 | 2/2011 | Soula et al. |
| 2011/0039773 A1 | 2/2011 | Alaoui-Ismaili et al. |
| 2011/0159068 A1 | 6/2011 | Soula et al. |
| 2011/0160441 A1 | 6/2011 | Ehringer et al. |
| 2011/0177135 A1 | 7/2011 | Rueger et al. |
| 2011/0184381 A1 | 7/2011 | Shintani |
| 2011/0224138 A1 | 9/2011 | Krop et al. |
| 2011/0224410 A1 | 9/2011 | Hile et al. |
| 2011/0253583 A1 | 10/2011 | Kadiyala |
| 2011/0280838 A1 | 11/2011 | Kramer et al. |
| 2011/0319328 A1 | 12/2011 | Ron |
| 2012/0028219 A1 | 2/2012 | Emerton et al. |
| 2012/0034577 A1 | 2/2012 | Chaar |
| 2012/0064043 A1 | 3/2012 | Ferguson et al. |
| 2012/0077743 A1 | 3/2012 | Rueger et al. |
| 2012/0114755 A1 | 5/2012 | Amadio et al. |
| 2012/0130386 A1 | 5/2012 | Mckay |
| 2012/0165257 A1 | 6/2012 | Byers et al. |
| 2012/0165731 A1 | 6/2012 | Byers et al. |
| 2012/0184490 A1 | 7/2012 | Murray et al. |
| 2012/0258917 A1 | 10/2012 | Goad et al. |
| 2012/0315698 A1 | 12/2012 | Harmon et al. |
| 2012/0322729 A1 | 12/2012 | Pohl et al. |

\* cited by examiner

```
GDF5-Trc      QEVKHMPLAT RQGKRPSKNL KARCSRKALH VNFKDMGWDD WIIAPLEYEA
GDF5-CofA           APSAT RQGKRPSKNL KARCSRKALH VNFKDMGWDD WIIAPLEYEA

GDF5-Trc      FHCEGLCEFP LRSHLEPTNH AVIQTLMNSM DPESTPPTCC VPTRLSPISI
GDF5-CofA     FHCEGLCEFP LRSHLEPTNH AVIQTLMNSM DPESTPPTCC VPTRLSPISI

GDF5-Trc      LFIDSANNVV YKQYEDMVVE SCGCR
GDF5-CofA     LFIDSANNVV YKQYEDMVVE SCGCR
```

Protein Alignment Program: BLASTP 2.2.27+

Score = 251 bits (640), Expect = 2e-91, Method: Compositional matrix adjust.
Identities = 118/119 (99%), Positives = 118/119 (99%), Gaps = 0/119 (0%)

```
GDF5-Trc      PLATRQGKRPSKNLKARCSRKALHVNFKDMGWDDWIIAPLEYEAFHCEGLCEFPLRSHLE  66
              P ATRQGKRPSKNLKARCSRKALHVNFKDMGWDDWIIAPLEYEAFHCEGLCEFPLRSHLE
GDF5-CofA     PSATRQGKRPSKNLKARCSRKALHVNFKDMGWDDWIIAPLEYEAFHCEGLCEFPLRSHLE  61

GDF5-Trc      PTNHAVIQTLMNSMDPESTPPTCCVPTRLSPISILFIDSANNVVYKQYEDMVVESCGCR  125
              PTNHAVIQTLMNSMDPESTPPTCCVPTRLSPISILFIDSANNVVYKQYEDMVVESCGCR
GDF5-CofA     PTNHAVIQTLMNSMDPESTPPTCCVPTRLSPISILFIDSANNVVYKQYEDMVVESCGCR  120
```

FIG. 1C

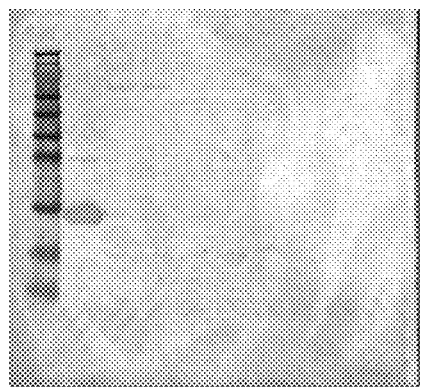
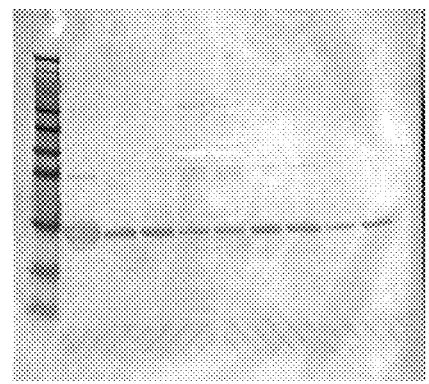
FIG. 3A    FIG. 3B
| Lane | Samples |
|---|---|
| 1 | Marker |
| 2 | GDF-5 Reference Material (3ug load) |
| 3 | GDF5-Trc + 1 (rec A) |
| 4 | GDF5-Trc + 3 (rec A) |
| 5 | GDF5-Trc + 1 (rec A O/N) |
| 6 | GDF5-Trc + 3 (rec A O/N) |
| 7 | GDF5-Trc + 1 (HMS) |
| 8 | GDF5-Trc + 3 (HMS) |
| 9 | GDF5-Trc + 1 (rec A) |
| 10 | GDF5-Trc + 1 (HMS) |
FIG. 3C

| Lane | Samples |
|---|---|
| 1 | Blank |
| 2 | SeeBlue MW Marker |
| 3 | 0.5μg GDF-5 Reference Material |
| 4 | GDF5-Trc + 1 (HMS) |
| 5 | GDF5-Trc + 2 (HMS) |
| 6 | GDF5-Trc + 3 (HMS) |
| 7 | GDF5-Trc + 4 (HMS) |
| 8 | GDF5-Trc + 5 (HMS) |
| 9 | GDF5-Trc - 3 (HMS) |
| 10 | Blank |

NuPage, 12% Bis-Tris Gel, 1.0 mm x 15 well, Reduced condition
1X MES Running Buffer

| Lane | Sample Description | Lane | Sample Description |
|---|---|---|---|
| 1 | Blank | 9 | SF020311D, GDF5-Trc (HMS) |
| 2 | Mark 12 MW Marker | 10 | PF020311A, GDF5-Trc (HMS) |
| 3 | 0.3 μg rhGDF-5 Reference Material | 11 | SF020311C, GDF5-Trc (HMS) |
| 4 | 3 μg rhGDF-5 Reference Material | 12 | PF020311D, GDF5-Trc (HMS) |
| 5 | SF020311A, GDF5-Trc (HMS) | 13 | Blank |
| 6 | PF020311B, GDF5-Trc (HMS) | 14 | Blank |
| 7 | PF020311C, GDF5-Trc (HMS) | 15 | Blank |
| 8 | SF020311B, GDF5-Trc (HMS) | | |

High Cell Density Media Formulation

| Trace metals | quantity/liter |
|---|---|
| Hydrochloric acid, (38%) | 14.7 |
| Calcium Chloride, dihydrate | 0.5 |
| Ferrous Sulfate, heptahydrate | 0.35 |
| Cobalt Chloride, hexahydrate | 0.15 |
| Manganese Sulfate, monohydrate | 0.08 |
| Cupric Sulfate, pentahydrate | 0.05 |
| Zinc Sulfate, heptahydrate | 0.05 |

| 6X Batch Media | |
|---|---|
| L-Leucine | 1.2 |
| L-Isoleucine | 1.2 |
| Proline | 1.2 |
| Citric Acid, Monohydrate | 12.6 |
| Glucose | 60 |
| Thiamine HCl | 0.3 |
| Ammonium Chloride | 12 |
| Magnesium Sulfate, heptahydrate | 1.5 |
| Potassium Phosphate, monobasic | 33 |
| Sodium Phosphate, dibasic, dodecahydrate | 86.4 |
| Trace metals stock (mL) | 100.2 |

| Feed media | |
|---|---|
| L-Leucine | 10 |
| L-Isoleucine | 4 |
| Proline | 10 |
| Citric Acid, Monohydrate | 3.3 |
| Glucose | 500 |
| Magnesium Sulfate, heptahydrate | 12 |
| Thiamine, HCl | 0.05 |
| Potassium Phosphate, monobasic | 9 |
| Sodium Phosphate, dibasic, dodecahydrate | 24 |
| Calcium Chloride, dihydrate | 0.4 |
| Ferrous Sulfate, heptahydrate | 0.3 |
| Cobalt Chloride, hexahydrate | 0.15 |
| Manganese Sulfate, tetrahydrate | 0.1 |
| Cupric Sulfate, pentahydrate | 0.5 |
| Zinc Sulfate, heptahydrate | 0.05 |

Other
EDTA 3Na Trihydrate
EDTA 4Na Trihydrate
Sodium Tetraborate
Ammonium Molybdate
Bacto Yeast Extract
Bacto Tryptone
Sulfuric acid
L-Methionine
Polyetherpolyole
Sodium Chloride
Urea

FIG. 7

Effects List for Band Amount

| | Term | Stdized Effects | Sum of Squares | % Contribution |
|---|---|---|---|---|
| ⌂ | Intercept | | | |
| M | A-Sodium Molybdate | 0.087 | 0.015 | 28.82 |
| M | B-Magnesium sulfate, Heptahydrate | 0.069 | 9.522E-003 | 18.34 |
| M | C-Sodium Chloride | 0.070 | 9.661E-003 | 18.61 |
| e | D-EDTA | -0.020 | 7.605E-004 | 1.46 |
| e | E-MOPS | -0.011 | 2.420E-004 | 0.47 |
| e | F-Amino Acids | -0.050 | 5.000E-003 | 9.63 |
| e | G-B Vitamins | 0.032 | 2.112E-003 | 4.07 |
| ~ | AB | | Aliased | |
| ~ | AC | | Aliased | |
| ~ | AD | | Aliased | |
| ~ | AE | | Aliased | |
| ~ | AF | | Aliased | |
| ~ | AG | | Aliased | |
| ~ | BC | | Aliased | |
| ~ | BD | | Aliased | |
| ~ | BE | | Aliased | |
| ~ | BF | | Aliased | |
| ~ | BG | | Aliased | |
| ~ | CD | | Aliased | |
| ~ | CE | | Aliased | |
| ~ | CF | | Aliased | |
| ~ | CG | | Aliased | |
| ~ | DE | | Aliased | |
| ~ | DF | | Aliased | |
| ~ | DG | | Aliased | |
| ~ | EF | | Aliased | |
| ~ | EG | | Aliased | |
| ~ | FG | | Aliased | |

Warning. Pure error terms not shown
Shapiro-Wilk test
W-value = 0.970
p-value = 0.842
A-Sodium Molybdate
B-Magnesium sulfate, Heptahydrate
C-Sodium Chloride
D-EDTA
E-MOPS
F-Amino Acids
G-B Vitamins
▫ Positive Effects
✱ Negative Effects

*FIG. 8B*

ANOVA for selected factorial model

Analysis of variance table [Partial sum of squares - Type III]

| Source | Sum of Square | df | Mean Square | F Value | p-value Prob > F | |
|---|---|---|---|---|---|---|
| Model | 0.034 | 3 | 0.011 | 5.12 | 0.0288 | significant |
| A-Sodium Molybdate | 0.015 | 1 | 0.015 | 6.74 | 0.0318 | |
| B-Magnesium sulfate | 9.522E-003 | 1 | 9.522E-003 | 4.29 | 0.0722 | |
| C-Sodium Chloride | 9.661E-003 | 1 | 9.661E-003 | 4.35 | 0.0705 | |
| Residual | 0.018 | 8 | 2.221E-003 | | | |
| Lack of Fit | 9.849E-003 | 5 | 1.970E-003 | 0.75 | 0.6396 | not significant |
| Pure Error | 7.922E-003 | 3 | 2.641E-003 | | | |
| Cor Total | 0.052 | 11 | | | | |
| Curvature | | | | 0.76 | 0.4131 | not significant (centerpoints removed from model) |

| | | | | |
|---|---|---|---|---|
| Std. Dev. | 0.047 | R-Squared | 0.6577 | |
| Mean | 0.093 | Adj R-Squared | 0.5294 | |
| C.V.% | 50.68 | Pred R-Squared | 0.2212 | |
| PRESS | 0.040 | Adeq Precision | 8.269 | |

| Factor | Coefficient Estimate | df | Standard Error | 95% CI Low | 95% CI High | VIF |
|---|---|---|---|---|---|---|
| Intercept | 0.093 | 1 | 0.014 | 0.062 | 0.12 | |
| A-Sodium Molybdate | 0.043 | 1 | 0.017 | 4.624E-003 | 0.082 | 1.00 |
| B-Magnesium sulfate | 0.035 | 1 | 0.017 | -3.926E-003 | 0.073 | 1.00 |
| C-Sodium Chloride | 0.035 | 1 | 0.017 | -3.676E-003 | 0.073 | 1.00 |

Final Equation in Terms of Actual Factors:

rhGDF = -0.14050
+0.017300 * Sodium Moylbdate
+0.017250 * Magnesium sulfate, Heptahydrate
+0.017375 * Sodium Chloride

*FIG. 8C*

Optimization of Response 2: Band Amount (relative pixels)

| | Term | Stdized Effects | Sum of Squares | % Contribution |
|---|---|---|---|---|
| ◒ | Intercept | | | |
| M | A-Sodium Molybdate | -0.099 | 6.103E-003 | 11.66 |
| M | B-Magnesium sulfate, Heptahydrate | 0.045 | 7.923E-003 | 15.17 |
| e | C-Sodium Chloride | -7.672E-003 | 2.354E-004 | 0.45 |
| e | D-EDTA | -0.037 | 5.473E-003 | 10.48 |
| e | E-MOPS | -4.553E-003 | 8.298E-005 | 0.16 |
| e | F-Amino Acids | 6.168E-003 | 1.522E-004 | 0.29 |
| e | G-B Vitamins | -0.021 | 1.811E-003 | 3.47 |
| M | H-Yeast extract | 0.050 | 9.979E-003 | 19.10 |
| e | J-Tryptone | -3.793E-003 | 5.754E-005 | 0.11 |
| e | AB | -0.035 | 4.797E-003 | 9.18 |
| e | AC | 0.014 | 7.573E-004 | 1.45 |
| e | AD | 0.026 | 2.749E-003 | 5.26 |
| e | AE | -0.017 | 1.135E-003 | 2.17 |
| ~ | AF | | Aliased | |
| e | AG | -6.942E-003 | 1.928E-004 | 0.37 |
| e | AH | -0.032 | 4.094E-003 | 7.64 |
| ~ | AJ | | Aliased | |
| ~ | BC | | Aliased | |
| ~ | BD | | Aliased | |
| ~ | BE | | Aliased | |
| ~ | BF | | Aliased | |
| ~ | BG | | Aliased | |
| ~ | BH | | Aliased | |

Warning. Pure error terms not shown
Shapiro-Wilk test
W-value = 0.959
p-value = 0.776
A: Sodium Molybdate
B: Magnesium sulfate, Heptahydrate
C: Sodium Chloride
D: EDTA
E: MOPS
F: Amino Acids
G: B Vitamins
H: Yeast extract
J: Tryptone
▫ Positive Effects
■ Negative Effects

*FIG. 9B*

ANOVA for selected factorial model

Analysis of variance table [Partial sum of squares - Type III]

| Source | Sum of Square | df | Mean Square | F Value | p-value Prob > F | |
|---|---|---|---|---|---|---|
| Model | 0.024 | 3 | 8.002E-003 | 4.65 | 0.0161 | significant |
| A-Sodium Molybdate | 6.103E-003 | 1 | 6.103E-003 | 3.54 | 0.0781 | |
| B-Magnesium sulfate | 7.923E-003 | 1 | 7.923E-003 | 4.60 | 0.0477 | |
| C-Sodium Chloride | 9.979E-003 | 1 | 9.979E-003 | 5.79 | 0.0285 | |
| Curvature | 6.795E-004 | 1 | 6.795E-004 | 0.39 | 0.5388 | not significant |
| Residual | 0.028 | 16 | 1.723E-003 | | | |
| Lack of Fit | 0.022 | 12 | 1.795E-003 | 1.19 | 0.4735 | not significant |
| Pure Error | 6.022E-003 | 4 | 1.505E-003 | | | |
| Cor Total | 0.052 | 20 | | | | |

| | | | | |
|---|---|---|---|---|
| Std. Dev. | 0.041 | R-Squared | 0.4595 | |
| Mean | 0.046 | Adj R-Squared | 0.3641 | |
| C.V.% | 89.17 | Pred R-Squared | 0.1520 | |
| PRESS | 0.044 | Adeq Precision | 7.505 | |

| Factor | Coefficient Estimate | df | Standard Error | 95% CI Low | 95% CI High | VIF |
|---|---|---|---|---|---|---|
| Intercept | 0.046 | 1 | 8.894E-003 | 0.027 | 0.064 | |
| A-Sodium Molybdate | -0.020 | 1 | 0.010 | -0.041 | 1.968E-003 | 1.00 |
| B-Magnesium sulfate | 0.022 | 1 | 0.010 | 7.555E-004 | 0.044 | 1.00 |
| C-Sodium Chloride | 0.025 | 1 | 0.010 | 3.476E-003 | 0.046 | 1.00 |

Final Equation in Terms of Actual Factors:

rhGDF band Amount = +0.034817
    -7.81191E-003 * Sodium Moylbdate
    +0.011127 * Magnesium sulfate
    +0.012487 * Yeast extract

*FIG. 9C*

Optimization of Response 2: Band Amount (relative pixels)

| | Term | Stdized Effects | Sum of Squares | % Contribution |
|---|---|---|---|---|
| 🔒 | Intercept | | | |
| e | A-Sodium Molybdate | -426.77 | 7.285E+005 | 0.067 |
| e | B-Magnesium sulfate, Heptahydrate | 423.80 | 7.184E+005 | 0.067 |
| M | C-Sodium Chloride | -3035.52 | 3.730E+007 | 3.45 |
| e | D-EDTA | -933.25 | 1.412E006 | 0.32 |
| M | E-MOPS | -5940.69 | 9.091E+005 | 13.07 |
| e | F-Amino Acids | 476.74 | 3.038E+006 | 0.084 |
| e | G-B Vitamins | 871.55 | 7.577E+008 | 0.28 |
| M | H-Yeast extract | 13762.77 | 7.323E+007 | 70.16 |
| M | J-Tryptone | 4278.79 | 2.394E+005 | 6.78 |
| e | AB | 244.62 | 6902.58 | 0.022 |
| e | AC | 41.54 | 19885.89 | 6.392E-004 |
| e | AD | 70.51 | 6.826E+005 | 1.841E-003 |
| e | AE | 413.08 | Aliased | 0.063 |
| ~ | AF | | 2.228E+006 | |
| e | AG | 746.31 | 6.191E+006 | 0.21 |
| e | AH | -1244.12 | Aliased | 0.57 |
| ~ | AJ | | Aliased | |
| ~ | BC | | Aliased | |
| ~ | BD | | Aliased | |
| ~ | BE | | Aliased | |
| ~ | BF | | Aliased | |

Warning. Pure error terms not shown
Shapiro-Wilk test
W-value = 0.907
p-value = 0.224
A: Sodium Molybdate
B: Magnesium sulfate, Heptahydrate
C: Sodium Chloride
D: EDTA
E: MOPS
F: Amino Acids
G: B Vitamins
H: Yeast extract
J: Tryptone
▫ Positive Effects
▪ Negative Effects

*FIG. 9E*

ANOVA for selected factorial model

Analysis of variance table [Partial sum of squares - Type III]

| Source | Sum of Square | df | Mean Square | F Value | p-value Prob > F | |
|---|---|---|---|---|---|---|
| Model | 1.009E+009 | 4 | 2.523E+008 | 188.73 | <0.0001 | significant |
| C-Sodium Chloride | 3.730E+007 | 1 | 3.730E+007 | 27.89 | <0.0001 | |
| E-MOPS | 1.412E+008 | 1 | 1.412E+008 | 105.59 | <0.0001 | |
| H-Yeast extract | 7.577E+008 | 1 | 7.577E+008 | 566.66 | <0.0001 | |
| J-Tryptone | 7.323E+007 | 1 | 7.323E+007 | 54.77 | <0.0001 | |
| Curvature | 5.055E+007 | 15 | 5.055E+007 | 37.81 | <0.0001 | significant |
| Residual | 2.006E+007 | 11 | 1.337E+006 | | | |
| Lack of Fit | 1.825E+007 | 4 | 1.659E+006 | 3.67 | 0.1105 | not significant |
| Pure Error | 1.810E+006 | 20 | 4.524E+005 | | | |
| Cor Total | 1.080E+009 | | | | | |

| | | | | |
|---|---|---|---|---|
| Std. Dev. | 2100.74 | R-Squared | 0.9346 | |
| Mean | 24278.38 | Adj R-Squared | 0.9183 | |
| C.V.% | 8.65 | Pred R-Squared | 0.9020 | |
| PRESS | 1.058E+008 | Adeq Precision | 23.396 | |

| Factor | Coefficient Estimate | df | Standard Error | 95% CI Low | 95% CI High | VIF |
|---|---|---|---|---|---|---|
| Intercept | 24278.38 | 1 | 456.42 | 23306.58 | 25250.19 | |
| C-Sodium Chloride | -1526.76 | 1 | 525.19 | -2640.10 | -413.41 | 1.00 |
| E-MOPS | -2970.35 | 1 | 525.19 | -4083.69 | -1857.00 | 1.00 |
| H-Yeast extract | 6881.39 | 1 | 525.19 | 5768.04 | 7994.73 | 1.00 |
| J-Tryptone | 2139.40 | 1 | 525.19 | 1026.05 | 3252.74 | 1.00 |

Final Equation in Terms of Actual Factors:

Biomass (AUC) = +19754.70654
　　　　　-763.37962　　* Sodium Chloride
　　　　　-59.40690　　* MOPS
　　　　　+3440.69266　* Yeast extract
　　　　　+1069.69863　* Tryptone

*FIG. 9F*

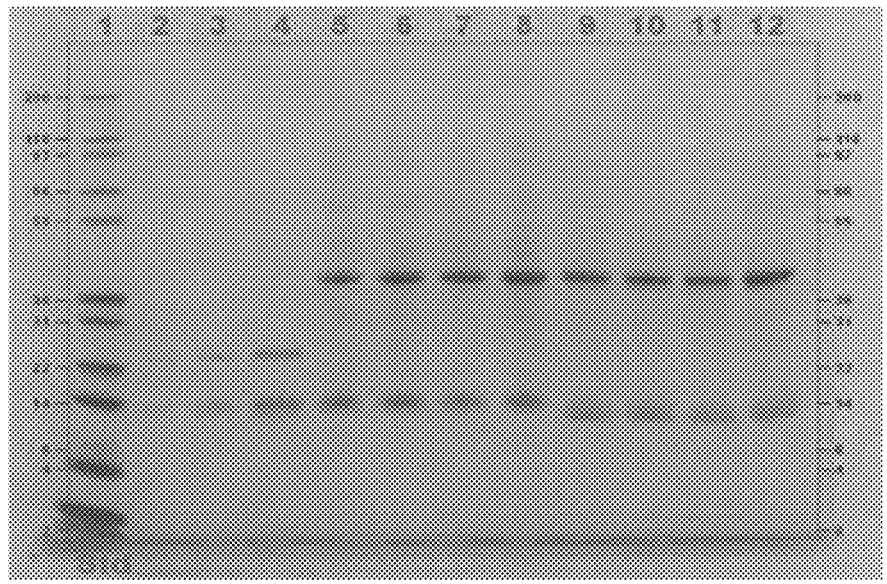

Condition A (pH 6.5)

| Lane | Load | Calculated GDF-5 by densitometry (mg/ml) |
|---|---|---|
| 1 | Mark 12 Ladder (7µL) | N/A |
| 2 | GDF-5, Not used due to irregularity | N/A |
| 3 | GDF-5, Not used due to irregularity | N/A |
| 4 | GDF-5, Not used due to irregularity | N/A |
| 5 | EFT 22, Red. ~9hrs Post-Ind. (10µL) | 2.8 |
| 6 | EFT 24, Red. ~11 hrs Post-Ind. (10µL) | 3.7 |
| 7 | EFT 26, Red. ~13 hrs Post-Ind. (10µL) | 3.1 |
| 8 | EFT 28, Red. ~15 hrs Post-Ind. (10µL) | 3.3 |
| 9 | EFT 22, Non-Red. ~9 hrs Post-Ind. (10µL) | N/A |
| 10 | EFT 24, Non-Red. ~11 hrs Post-Ind. (10µL) | N/A |
| 11 | EFT 26, Non-Red. ~13 hrs Post-Ind. (10µL) | N/A |
| 12 | EFT 28, Non-Red. ~15 hrs Post-Ind. (10µL) | N/A |

*FIG. 11A*

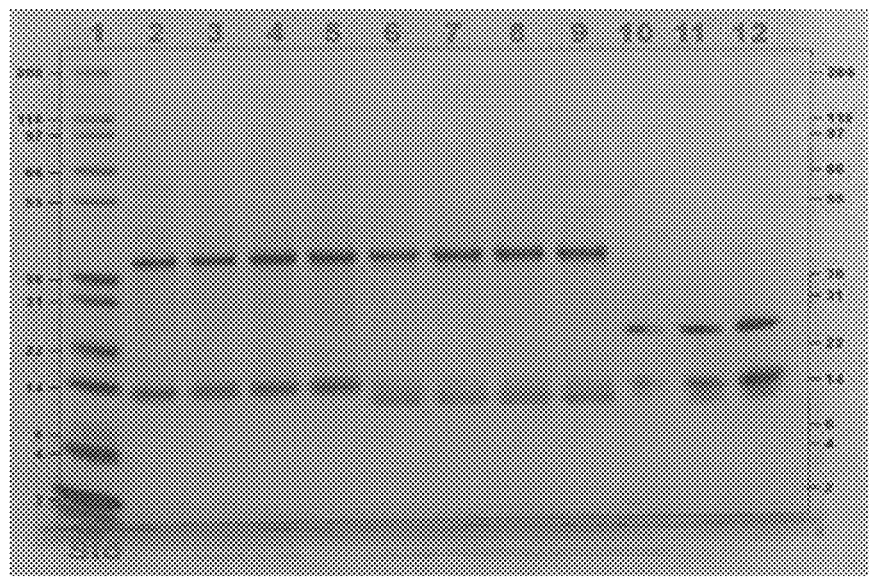

Condition B (pH 7.1)

| Lane | Load | Calculated GDF-5 by densitometry (mg/ml) |
|---|---|---|
| 1 | Mark 12 Ladder (7µL) | N/A |
| 2 | EFT 22, Red. ~9hrs Post-Ind. (10µL) | 4.2 |
| 3 | EFT 24, Red. ~11 hrs Post-Ind. (10µL) | 4.6 |
| 4 | EFT 26, Red. ~13 hrs Post-Ind. (10µL) | 5.2 |
| 5 | EFT 28, Red. ~15 hrs Post-Ind. (10µL) | 5.0 |
| 6 | EFT 22, Non-Red. ~9 hrs Post-Ind. (10µL) | N/A |
| 7 | EFT 24, Non-Red. ~11 hrs Post-Ind. (10µL) | N/A |
| 8 | EFT 26, Non-Red. ~13 hrs Post-Ind. (10µL) | N/A |
| 9 | EFT 28, Non-Red. ~15 hrs Post-Ind. (10µL) | N/A |
| 10 | GDF-5, Not used due to irregularity | N/A |
| 11 | GDF-5, Not used due to irregularity | N/A |
| 12 | GDF-5, Not used due to irregularity | N/A |

*FIG. 11B*

Condition C (Low Oxygen, pH 6.8)

| Lane | Load | Calculated GDF-5 by densitometry (mg/ml) |
|---|---|---|
| 1 | Mark 12 Ladder (7μL) | N/A |
| 2 | EFT 22, Red. ~9hrs Post-Ind. (10μL) | 2.7 |
| 3 | EFT 24, Red. ~11 hrs Post-Ind. (10μL) | 1.7 |
| 4 | EFT 26, Red. ~13 hrs Post-Ind. (10μL) | 2.2 |
| 5 | EFT 28, Red. ~15 hrs Post-Ind. (10μL) | 1.9 |
| 6 | GDF-5, 0.40μg load | N/A |
| 7 | GDF-5, 0.80μg load | N/A |
| 8 | GDF-5, 1.60μg load | N/A |
| 9 | EFT 22, Non-Red. ~9hrs Post-Ind. (10μL) | N/A |
| 10 | EFT 24, Non-Red. ~11 hrs Post-Ind. (10μL) | N/A |
| 11 | EFT 26, Non-Red. ~13 hrs Post-Ind. (10μL) | N/A |
| 12 | EFT 28, Non-Red. ~15 hrs Post-Ind. (10μL) | N/A |

SEQUENCE LISTING

<160> NUMBER OF SEQ ID NOS: 39

<210> SEQ ID NO 1
<211> LENGTH: 528
<212> TYPE: DNA
<213> ORGANISM: human

<400> SEQUENCE: 1

```
ctcgagttag cgacagccgc agctctccac caccatatct tcgtactgct tgtaaacaac      60
attgttcgcg ctatcgatga acagaataga gatcgggctc agacgggtcg gaacacagca     120
ggtaggcggc gtgctctccg ggtccatcga attcatcaac gtctggatga ctgcatggtt     180
agtcggctcc agatggctac gcagcggaaa ctcgcacaga ccctcacagt gaaaagcttc     240
atattccagc ggcgcaataa tccagtcatc ccaacccatg tctttgaaat tgacgtgcag     300
ggcttttacg gagcaacgcg ccttcaggtt cttgcttggt cttttgcctt ggcgggttgc     360
gagcggcata tgttttacct cctgttaaac aaaattattt ctagagggaa accgttgtgg     420
```

| | | |
|---|---|---|
| aattgtgagc gctcacaatt ccacaattat acgagccgga tgattaattg tcaacacact | 480 | |
| gtgcatgaag ctcgtaattg ttatccgctc acaattaagg gcgacaca | 528 | |

<210> SEQ ID NO 2
<211> LENGTH: 4299
<212> TYPE: DNA
<213> ORGANISM: human

<400> SEQUENCE: 2

| | |
|---|---|
| ctcatgacca aaatccctta acgtgagtta cgcgcgcgtc gttccactga gcgtcagacc | 60 |
| ccgtagaaaa gatcaaagga tcttcttgag atccttttttt tctgcgcgta atctgctgct | 120 |
| tgcaaacaaa aaaaccaccg ctaccagcgg tggtttgttt gccggatcaa gagctaccaa | 180 |
| ctctttttcc gaaggtaact ggcttcagca gagcgcagat accaaatact gttcttctag | 240 |
| tgtagccgta gttagcccac cacttcaaga actctgtagc accgcctaca tacctcgctc | 300 |
| tgctaatcct gttaccagtg gctgctgcca gtggcgataa gtcgtgtctt accgggttgg | 360 |
| actcaagacg atagttaccg gataaggcgc agcggtcggg ctgaacgggg ggttcgtgca | 420 |
| cacagcccag cttggagcga acgacctaca ccgaactgag atacctacag cgtgagctat | 480 |
| gagaaagcgc cacgcttccc gaagggagaa aggcggacag gtatccggta agcggcaggg | 540 |
| tcggaacagg agagcgcacg agggagcttc caggggggaaa cgcctggtat ctttatagtc | 600 |
| ctgtcgggtt tcgccacctc tgacttgagc gtcgattttt gtgatgctcg tcagggggggc | 660 |
| ggagcctatg gaaaaacgcc agcaacgcgg cctttttacg gttcctggcc ttttgctggc | 720 |
| cttttgctca catgttcttt cctgcgttat cccctgattc tgtggataac cgtattaccg | 780 |
| cctttgagtg agctgatacc gctcgccgca gccgaacgac cgagcgcagc gagtcagtga | 840 |
| gcgaggaagc ggaaggcgag agtagggaac tgccaggcat caaactaagc agaaggcccc | 900 |
| tgacggatgg cctttttgcg tttctacaaa ctctttctgt gttgtaaaac gacggccagt | 960 |
| cttaagctcg ggccccctgg gcggttctga taacgagtaa tcgttaatcc gcaaataacg | 1020 |
| taaaaacccg cttcggcggg ttttttatg ggggagttt agggaaagag catttgtcag | 1080 |
| aatatttaag ggcgcctgtc actttgcttg atatatgaga attatttaac cttataaatg | 1140 |
| agaaaaaagc aacgcacttt aaataagata cgttgctttt tcgattgatg aacacctata | 1200 |
| attaaactat tcatctatta tttatgattt tttgtatata caatatttct agtttgttaa | 1260 |
| agagaattaa gaaaataaat ctcgaaaata ataagggaa aatcagtttt tgatatcaaa | 1320 |
| attatacatg tcaacgataa tacaaaatat aatacaaact ataagatgtt atcagtatt | 1380 |
| attatgcatt tagaataaat tttgtgtcgc ccttaattgt gagcggataa caattacgag | 1440 |
| cttcatgcac agtgaaatca tgaaaaattt atttgctttg tgagcggata acaattataa | 1500 |
| tatgtggaat tgtgagcgct cacaattcca caacggtttc cctctagaaa taattttgtt | 1560 |
| taacttttag gaggtaaaac atatgccgct cgcaacccgc caaggcaaaa gaccaagcaa | 1620 |
| gaacctgaag gcgcgttgct cccgtaaagc cctgcacgtc aatttcaaag acatgggttg | 1680 |
| ggatgactgg attattgcgc cgctggaata tgaagctttt cactgtgagg gtctgtgcga | 1740 |
| gtttccgctg cgtagccatc tggagccgac taaccatgca gtcatccaga cgttgatgaa | 1800 |
| ttcgatggac ccggagagca cgccgcctac ctgctgtgtt ccgacccgtc tgagcccgat | 1860 |
| ctctattctg ttcatcgata gcgcgaacaa tgttgtttac aagcagtacg aagatatggt | 1920 |
| ggtgagagc tgcggctgtc gctaactcga gccccaaggg cgacacccccc taattagccc | 1980 |
| gggcgaaagg cccagtcttt cgactgagcc tttcgtttta tttgatgcct ggcagttccc | 2040 |

```
tactctcgca tggggagtcc ccacactacc atcggcgcta cggcgtttca cttctgagtt      2100
cggcatgggg tcaggtggga ccaccgcgct actgccgcca ggcaaacaag gggtgttatg      2160
agccatattc aggtataaat gggctcgcga taatgttcag aattggttaa ttggttgtaa      2220
cactgacccc tatttgttta tttttctaaa tacattcaaa tatgtatccg ctcatgagac      2280
aataaccctg ataaatgctt caataatatt gaaaaggaa gaatatgagc catattcaac      2340
gggaaacgtc gaggccgcga ttaaattcca acatggatgc tgatttatat gggtataaat      2400
gggctcgcga taatgtcggg caatcaggtg cgacaatcta tcgcttgtat gggaagcccg      2460
atgcgccaga gttgtttctg aaacatggca aaggtagcgt tgccaatgat gttacagatg      2520
agatggtcag actaaactgg ctgacggaat ttatgccact tccgaccatc aagcatttta      2580
tccgtactcc tgatgatgca tggttactca ccactgcgat ccccggaaaa acagcgttcc      2640
aggtattaga agaatatcct gattcaggtg aaaatattgt tgatgcgctg gcagtgttcc      2700
tgcgccggtt gcactcgatt cctgtttgta attgtccttt taacagcgat cgcgtatttc      2760
gcctcgctca ggcgcaatca cgaatgaata cggtttggt tgatgcgagt gattttgatg      2820
acgagcgtaa tggctggcct gttgaacaag tctggaaaga atgcataaa cttttgccat      2880
tctcaccgga ttcagtcgtc actcatggtg atttctcact tgataacctt attttgacg      2940
aggggaaatt aataggttgt attgatgttg gacgagtcgg aatcgcagac cgataccagg      3000
atcttgccat cctatggaac tgcctcggtg agttttctcc ttcattacag aaacggcttt      3060
ttcaaaaata tggtattgat aatcctgata tgaataaatt gcagtttcat ttgatgctcg      3120
atgagttttt ctaagcggcg cgccatcgaa tggcgcaaaa cctttcgcgg tatggcatga      3180
tagcgcccgg aagagagtca attcaggtgt gtgaatatga aaccagtaac gttatacgat      3240
gtcgcagagt atgccggtgt ctcttatcag accgtttccc gcgtggtgaa ccaggccagc      3300
cacgtttctg cgaaaacgcg ggaaaaagtg gaagcggcga tggcggagct gaattacatt      3360
cccaaccgcg tggcacaaca actggcgggc aaacagtcgt tgctgattgg cgttgccacc      3420
tccagtctgg ccctgcacgc gccgtcgcaa attgtcgcgg cgattaaatc tcgcgccgat      3480
caactgggtg ccagcgtggt ggtgtcgatg gtagaacgaa gcggcgtcga agcctgtaaa      3540
gcggcggtgc acaatcttct cgcgcaacgc gtcagtgggc tgatcattaa ctatccgctg      3600
gatgaccagg atgccattgc tgtggaagct gcctgcacta atgttccggc gttatttctt      3660
gatgtctctg accagacacc catcaacagt attattttct cccatgagga cggtacgcga      3720
ctgggcgtgg agcatctggt cgcattgggt caccagcaaa tcgcgctgtt agcgggccca      3780
ttaagttctg tctcggcgcg tctgcgtctg gctggctggc ataaatatct cactcgcaat      3840
caaattcagc cgatagcgga acgggaaggc gactggagtg ccatgtccgg ttttcaacaa      3900
accatgcaaa tgctgaatga gggcatcgtt cccactgcga tgctggttgc caacgatcag      3960
atggcgctgg gcgcaatgcg cgccattacc gagtccgggc tgcgcgttgg tgcggatatc      4020
tcggtagtgg gatacgacga taccgaagat agctcatgtt atatcccgcc gttaaccacc      4080
atcaaacagg attttcgcct gctggggcaa accagcgtgg accgcttgct gcaactctct      4140
cagggccagg cggtgaaggg caatcagctg ttgccagtct cactggtgaa aagaaaaacc      4200
accctggcgc ccaatacgca aaccgcctct ccccgcgcgt tggccgattc attaatgcag      4260
ctggcacgac aggtttcccg actggaaagc gggcagtga                             4299
```

<210> SEQ ID NO 3

<211> LENGTH: 4403
<212> TYPE: DNA
<213> ORGANISM: Homo sapiens

<400> SEQUENCE: 3

```
tattcaccac cctgaattga ctctcttccg ggcgctatca tgccataccg cgaaaggttt      60
tgcgccattc gatggcgcgc cgcttagaaa aactcatcga gcatcaaatg aaattgcaat     120
ttattcatat caggattatc aataccatat ttttgaaaaa gccgtttctg taatgaagga     180
gaaaactcac cgaggcagtt ccataggatg gcaagatcct ggtatcggtc tgcgattccg     240
actcgtccaa catcaataca acctattaat ttcccctcgt caaaaataag gttatcaagt     300
gagaaatcac catgagtgac gactgaatcc ggtgagaatg gcaaaagttt atgcatttct     360
ttccagactt gttcaacagg ccagccatta cgctcgtcat caaaatcact cgcatcaacc     420
aaaccgttat tcattcgtga ttgcgcctga gcgaggcgaa atacgcgatc gctgttaaaa     480
ggacaattac aaacaggaat cgagtgcaac cggcgcagga acactgccag cgcatcaaca     540
atattttcac ctgaatcagg atattcttct aatacctgga acgctgtttt tccgggatc      600
gcagtggtga gtaaccatgc atcatcagga gtacggataa aatgcttgat ggtcggaagt     660
ggcataaatt ccgtcagcca gtttagtctg accatctcat ctgtaacatc attggcaacg     720
ctacctttgc catgtttcag aaacaactct ggcgcatcgg gcttcccata caagcgatag     780
attgtcgcac ctgattgccc gacattatcg cgagcccatt tatacccata taatcagca     840
tccatgttgg aatttaatcg cggcctcgac gtttcccgtt gaatatggct catattcttc     900
cttttttcaat attattgaag catttatcag ggttattgtc tcatgagcgg atacatattt     960
gaatgtattt agaaaaataa acaaataggg gtcagtgtta caaccaatta accaattctg    1020
aacattatcg cgagcccatt tatacctgaa tatggctcat aacaccccttt gtttgcctgg    1080
cggcagtagc gcggtggtcc cacctgaccc catgccgaac tcagaagtga acgccgtag     1140
cgccgatggt agtgtgggga ctccccatgc gagagtaggg aactgccagg catcaaataa    1200
aacgaaaggc tcagtcgaaa gactgggcct ttcgcccggg ctaattaggg ggtgtcgccc    1260
ttattcgact ctatagtgaa gttcctattc tctagaaagt ataggaactt ctgaagtggg    1320
gctcgagtta gcgacagccg cagctctcca ccaccatatc ttcgtactgc ttgtaaacaa    1380
cattgttcgc gctatcgatg aacagaatag agatcgggct cagacgggtc ggaacacagc    1440
aggtaggcgg cgtgctctcc gggtccatcg aattcatcaa cgtctggatg actgcatggt    1500
tagtcggctc cagatggcta cgcagcggaa actcgcacag accctcacag tgaaaagctt    1560
catattccag cggcgcaata atccagtcat cccaacccat gtctttgaaa ttgacgtgca    1620
gggctttacg ggagcaacgc gccttcaggt tcttgcttgg tcttttgcct tggcgggttg    1680
cgagcggcat atgttttacc tcctgttaaa caaaattatt tctagaggga aaccgttgtg    1740
gaattgtgag cgctcacaat tccacaatta tacgagccgg atgattaatt gtcaacacac    1800
tgtgcatgaa gctcgtaatt gttatccgct cacaattaag ggcgacacaa atgaagtga     1860
agttcctata ctttctagag aataggaact tctatagtga gtcgaataag ggcgacacaa    1920
aattattct aaatgcataa taaatactga taacatctta tagtttgtat tatattttgt    1980
attatcgttg acatgtataa ttttgatatc aaaaactgat tttcccttta ttattttcga    2040
gatttatttt cttaattctc tttaacaaac tagaaatatt gtatatacaa aaaatcataa    2100
ataatagatg aatagtttaa ttataggtgt tcatcaatcg aaaaagcaac gtatcttatt    2160
taaagtgcgt tgcttttttc tcatttataa ggttaaataa ttctcatata tcaagcaaag    2220
```

```
tgacaggcgc ccttaaatat tctgacaaat gctctttccc taaactcccc ccataaaaaa    2280
acccgccgaa gcgggttttt acgttatttg cggattaacg attactcgtt atcagaaccg    2340 cccaggggc ccgagcttaa gactggccgt cgttttacaa cacagaaaga gtttgtagaa     2400
acgcaaaaag gccatccgtc aggggccttc tgcttagttt gatgcctggc agttccctac    2460
tctcgccttc cgcttcctcg ctcactgact cgctgcgctc ggtcgttcgg ctgcggcgag    2520
cggtatcagc tcactcaaag gcggtaatac ggttatccac agaatcaggg gataacgcag    2580
gaaagaacat gtgagcaaaa ggccagcaaa aggccaggaa ccgtaaaaag gccgcgttgc    2640
tggcgttttt ccataggctc cgcccccctg acgagcatca caaaaatcga cgctcaagtc    2700
agaggtggcg aaacccgaca ggactataaa gataccaggc gtttccccct ggaagctccc    2760
tcgtgcgctc tcctgttccg accctgccgc ttaccggata cctgtccgcc tttctccctt    2820
cgggaagcgt ggcgctttct catagctcac gctgtaggta tctcagttcg gtgtaggtcg    2880
ttcgctccaa gctgggctgt gtgcacgaac cccccgttca gcccgaccgc tgcgccttat    2940
ccggtaacta tcgtcttgag tccaacccgg taagacacga cttatcgcca ctggcagcag    3000
ccactggtaa caggattagc agagcgaggt atgtaggcgg tgctacagag ttcttgaagt    3060
ggtgggctaa ctacggctac actagaagaa cagtatttgg tatctgcgct ctgctgaagc    3120
cagttacctt cggaaaaaga gttggtagct cttgatccgg caaacaaacc accgctggta    3180
gcggtggttt ttttgtttgc aagcagcaga ttacgcgcag aaaaaaagga tctcaagaag    3240
atcctttgat cttttctacg ggtctgacgc tcagtggaa cgacgcgcgc gtaactcacg    3300
ttaagggatt ttggtcatga gtcactgccc gctttccagt cgggaaacct gtcgtgccag    3360
ctgcattaat gaatcggcca acgcgcgggg agaggcggtt tgcgtattgg gcgccagggt    3420
ggtttttctt ttcaccagtg agactggcaa cagctgattg cccttcaccg cctggccctg    3480
agagagttgc agcaagcggt ccacgctggt ttgccccagc aggcgaaaat cctgtttgat    3540
ggtggttaac ggcgggatat aacatgagct atcttcggta tcgtcgtatc ccactaccga    3600
gatatccgca ccaacgcgca gcccggactc ggtaatggcg cgcattgcgc ccagcgccat    3660
ctgatcgttg gcaaccagca tcgcagtggg aacgatgccc tcattcagca tttgcatggt    3720
ttgttgaaaa ccggacatgg cactccagtc gccttcccgt tccgctatcg gctgaatttg    3780
attgcgagtg agatatttat gccagccagc cagacgcaga cgcgccgaga cagaacttaa    3840
tgggcccgct aacagcgcga tttgctggtg acccaatgcg accagatgct ccacgcccag    3900
tcgcgtaccg tcctcatggg agaaaataat actgttgatg ggtgtctggt cagagacatc    3960
aagaaataac gccggaacat tagtgcaggc agcttccaca gcaatggcat cctggtcatc    4020
cagcggatag ttaatgatca gcccactgac gcgttgcgcg agaagattgt gcaccgccgc    4080
tttacaggct tcgacgccgc ttcgttctac catcgacacc accacgctgg cacccagttg    4140
atcggcgcga gatttaatcg ccgcgacaat ttgcgacggc gcgtgcaggg ccagactgga    4200
ggtggcaacg ccaatcagca acgactgttt gcccgccagt tgttgtgcca gcgcggttggg    4260 aatgtaattc agctccgcca tcgccgcttc cacttttttcc cgcgttttcg cagaaacgtg    4320
gctggcctgg ttcaccacgc gggaaacggt ctgataagag acaccggcat actctgcgac    4380
atcgtataac gttactggtt tca                                            4403
```

<210> SEQ ID NO 4
<211> LENGTH: 125
<212> TYPE: PRT

-continued

<213> ORGANISM: Homo sapiens

<400> SEQUENCE: 4

Gln Glu Val Lys His Met Pro Leu Ala Thr Arg Gln Gly Lys Arg Pro
1               5                   10                  15

Ser Lys Asn Leu Lys Ala Arg Cys Ser Arg Lys Ala Leu His Val Asn
            20                  25                  30

Phe Lys Asp Met Gly Trp Asp Asp Trp Ile Ile Ala Pro Leu Glu Tyr
        35                  40                  45

Glu Ala Phe His Cys Glu Gly Leu Cys Glu Phe Pro Leu Arg Ser His
    50                  55                  60

Leu Glu Pro Thr Asn His Ala Val Ile Gln Thr Leu Met Asn Ser Met
65                  70                  75                  80

Asp Pro Glu Ser Thr Pro Pro Thr Cys Cys Val Pro Thr Arg Leu Ser
                85                  90                  95

Pro Ile Ser Ile Leu Phe Ile Asp Ser Ala Asn Asn Val Val Tyr Lys
            100                 105                 110

Gln Tyr Glu Asp Met Val Val Glu Ser Cys Gly Cys Arg
        115                 120                 125

<210> SEQ ID NO 5
<211> LENGTH: 120
<212> TYPE: PRT
<213> ORGANISM: human

<400> SEQUENCE: 5

Ala Pro Ser Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 6
<211> LENGTH: 4405
<212> TYPE: DNA
<213> ORGANISM: human

<400> SEQUENCE: 6
tattcaccac cctgaattga ctctcttccg ggcgctatca tgccataccg cgaaaggttt      60
tgcgccattc gatggcgcgc cgcttttaga aaaactcatc gagcatcaaa tgaaactgca     120
atttattcat atcaggatta tcaataccat atttttgaaa aagccgtttc tgtaatgaag     180
gagaaaactc accgaggcag ttccatagga tggcaagatc ctggtatcgg tctgcgattc     240
cgactcgtcc aacatcaata caacctatta atttccctc gtcaaaaata aggttatcaa      300
gtgagaaatc accatgagtg acgactgaat ccggtgagaa tggcaaaagt ttatgcattt     360

```
cttttccagac ttgttcaaca ggccagccat tacgctcgtc atcaaaatca ctcgcatcaa    420
ccaaaccgtt attcattcgt gattgcgcct gagcgaggcg aaatacgcga tcgctgttaa    480
aaggacaatt acaaacagga atcgagtgca accggcgcag gaacactgcc agcgcatcaa    540
caatattttc acctgaatca ggatattctt ctaatacctg gaacgctgtt tttccgggga    600
tcgcagtggt gagtaaccat gcatcatcag gagtacggat aaaatgcttg atggtcggaa    660
gtggcataaa ttccgtcagc cagtttagtc tgaccatctc atctgtaaca tcattggcaa    720
cgctaccttt gccatgtttc agaaacaact ctggcgcatc gggcttccca tacaagcgat    780
agattgtcgc acctgattgc ccgacattat cgcgagccca tttataccca tataaatcag    840
catccatgtt ggaatttaat cgcggcctcg acgtttcccg ttgaatatgg ctcatattct    900 tccttttttca atattattga agcatttatc agggttattg tctcatgagc ggatacatat    960
ttgaatgtat ttagaaaaat aaacaaatag gggtcagtgt acaaccaat taaccaattc    1020 tgaacattat cgcgagccca tttataccctg aatatggctc ataacacccc ttgtttgcct    1080
ggcggcagta gcgcggtggt cccacctgac cccatgccga actcagaagt gaaacgccgt    1140
agcgccgatg gtagtgtggg gactcccccat gcgagagtag ggaactgcca ggcatcaaat    1200
aaaacgaaag gctcagtcga aagactgggc ctttcgcccg gctaattag ggggtgtcgc    1260 ccttattcga ctctatagtg aagttcctat tctctagaaa gtataggaac ttctgaagtg    1320
gggctcgagt tagcgacagc cgcagctctc caccaccata tcttcgtact gcttgtaaac    1380
aacattgttc gcgctatcga tgaacagaat agagatcggg ctcagacggg tcggaacaca    1440
gcaggtaggc ggcgtgctct ccgggtccat cgaattcatc aacgtctgga tgactgcatg    1500
gttagtcggc tccagatggc tacgcagcgg aaactcgcac agaccctcac agtgaaaagc    1560
ttcatattcc agcggcgcaa taatccagtc atcccaaccc atgtctttga aattgacgtg    1620
cagggcttta cgggagcaac gcgccttcag gttcttgctt ggtcttttgc cttggcgggt    1680
tgcgagcggc atatgttta cctcctgtta aacaaaatta tttctagagg gaaaccgttg    1740
tggaattgtg agcgctcaca attccacaat tatacgagcc ggatgattaa ttgtcaacac    1800
actgtgcatg aagctcgtaa ttgttatccg ctcacaatta agggcgacac aaaatgaagt    1860
gaagttccta tactttctag agaataggaa cttctatagt gagtcgaata agggcgacac    1920
aaaatttatt ctaaatgcat aataaatact gataacatct tatagtttgt attatatttt    1980
gtattatcgt tgacatgtat aattttgata tcaaaaactg attttcccctt tattattttc    2040 gagatttatt ttcttaattc tctttaacaa actagaaata ttgtatatac aaaaaatcat    2100
aaataataga tgaatagttt aattataggt gttcatcaat cgaaaaagca acgtatctta    2160
tttaaagtgc gttgcttttt tctcatttat aaggttaaat aattctcata tatcaagcaa    2220
agtgacaggc gcccttaaat attctgacaa atgctctttc cctaaactcc ccccataaaa    2280
aaacccgccg aagcgggttt ttacgttatt tgcggattaa cgattactcg ttatcagaac    2340
cgcccagggg gcccgagctt aagactggcc gtcgttttac aacacagaaa gagtttgtag    2400
aaacgcaaaa aggccatccg tcagggggcct tctgcttagt ttgatgcctg gcagttccct    2460
actctcgcct tccgcttcct cgctcactga ctcgctgcgc tcggtcgttc ggctgcggcg    2520
agcggtatca gctcactcaa aggcggtaat acggttatcc acagaatcag gggataacgc    2580
aggaaagaac atgtgagcaa aaggccagca aaaggccagg aaccgtaaaa aggccgcgtt    2640
gctggcgttt ttccataggc tccgcccccc tgacgagcat cacaaaaatc gacgctcaag    2700
```

-continued

```
tcagaggtgg cgaaacccga caggactata aagataccag gcgtttcccc ctggaagctc    2760
cctcgtgcgc tctcctgttc cgaccctgcc gcttaccgga tacctgtccg cctttctccc    2820
ttcgggaagc gtggcgcttt ctcatagctc acgctgtagg tatctcagtt cggtgtaggt    2880
cgttcgctcc aagctgggct gtgtgcacga acccccgtt cagcccgacc gctgcgcctt    2940
atccggtaac tatcgtcttg agtccaaccc ggtaagacac gacttatcgc cactggcagc    3000
agccactggt aacaggatta gcagagcgag gtatgtaggc ggtgctacag agttcttgaa    3060
gtggtgggct aactacggct acactagaag aacagtattt ggtatctgcg ctctgctgaa    3120
gccagttacc ttcggaaaaa gagttggtag ctcttgatcc ggcaaacaaa ccaccgctgg    3180
tagcggtggt ttttttgttt gcaagcagca gattacgcgc agaaaaaaag gatctcaaga    3240
agatcctttg atcttttcta cggggtctga cgctcagtgg aacgacgcgc gcgtaactca    3300
cgttaaggga ttttggtcat gagtcactgc ccgctttcca gtcgggaaac ctgtcgtgcc    3360
agctgcatta atgaatcggc caacgcgcgg ggagaggcgg tttgcgtatt gggcgccagg    3420 gtggttttc ttttcaccag tgagactggc aacagctgat gcccttcac cgcctggccc    3480 tgagagagtt gcagcaagcg gtccacgctg gtttgcccca gcaggcgaaa atcctgtttg    3540
atggtggtta acggcgggat ataacatgag ctatcttcgg tatcgtcgta tcccactacc    3600
gagatatccg caccaacgcg cagcccggac tcggtaatgg cgcgcattgc gcccagcgcc    3660
atctgatcgt tggcaaccag catcgcagtg gaacgatgc cctcattcag catttgcatg    3720
gtttgttgaa aaccggacat ggcactccag tcgccttccc gttccgctat cggctgaatt    3780
tgattgcgag tgagatattt atgccagcca gccagacgca gacgcgccga gacagaactt    3840
aatgggcccg ctaacagcgc gatttgctgg tgacccaatg cgaccagatg ctccacgccc    3900
agtcgcgtac cgtcctcatg ggagaaaata atactgttga tgggtgtctg gtcagagaca    3960
tcaagaaata acgccggaac attagtgcag gcagcttcca cagcaatggc atcctggtca    4020
tccagcggat agttaatgat cagcccactg acgcgttgcg cgagaagatt gtgcaccgcc    4080
gctttacagg cttcgacgcc gcttcgttct accatcgaca ccaccacgct ggcacccagt    4140
tgatcggcgc gagatttaat cgccgcgaca atttgcgacg gcgcgtgcag gccagactg    4200 gaggtggcaa cgccaatcag caacgactgt ttgcccgcca gttgttgtgc cacgcggttg    4260
ggaatgtaat tcagctccgc catcgccgct tccactttt cccgcgtttt cgcagaaacg    4320
tggctggcct ggttcaccac gcgggaaacg gtctgataag agacaccggc atactctgcg    4380
acatcgtata acgttactgg tttca                                           4405
```

<210> SEQ ID NO 7
<211> LENGTH: 528
<212> TYPE: DNA
<213> ORGANISM: human

<400> SEQUENCE: 7

```
tgtgtcgccc ttaattgtga gcggataaca attacgagct tcatgcacag tgtgttgaca     60
attaatcatc cggctcgtat aattgtggaa ttgtgagcgc tcacaattcc acaacggttt    120
ccctctagaa ataattttgt ttaacaggag gtaaaacata tgccgctcgc aacccgccaa    180
ggcaaaagac caagcaagaa cctgaaggcg cgttgctccc gtaaagccct gcacgtcaat    240
ttcaaagaca tgggttggga tgactggatt attgcgccgc tggaatatga agcttttcac    300
tgtgagggtc tgtgcgagtt tccgctgcgt agccatctgg agccgactaa ccatgcagtc    360
atccagacgt tgatgaattc gatggaccgc gagagcacgc cgcctacctg ctgtgttccg    420
```

```
acccgtctga gcccgatctc tattctgttc atcgatagcg cgaacaatgt tgtttacaag    480
cagtacgaag atatggtggt ggagagctgc ggctgtcgct aactcgag                 528

<210> SEQ ID NO 8
<211> LENGTH: 21
<212> TYPE: DNA
<213> ORGANISM: Artificial Sequence
<220> FEATURE:
<223> OTHER INFORMATION: MDP1.1SF1-A, forward primer

<400> SEQUENCE: 8
ctatcatgcc ataccgcgaa a                                              21

<210> SEQ ID NO 9
<211> LENGTH: 19
<212> TYPE: DNA
<213> ORGANISM: Artificial Sequence
<220> FEATURE:
<223> OTHER INFORMATION: MDP1.2SF1-A, forward primer

<400> SEQUENCE: 9
gccagccatt acgctcgtc                                                 19

<210> SEQ ID NO 10
<211> LENGTH: 21
<212> TYPE: DNA
<213> ORGANISM: Artificial Sequence
<220> FEATURE:
<223> OTHER INFORMATION: MDP1.3SF1-A, forward primer

<400> SEQUENCE: 10
cgctaccttt gccatgtttc a                                              21

<210> SEQ ID NO 11
<211> LENGTH: 17
<212> TYPE: DNA
<213> ORGANISM: Artificial Sequence
<220> FEATURE:
<223> OTHER INFORMATION: MDP1.4SF1-A, forward primer

<400> SEQUENCE: 11
taatcgcggc ctcgacg                                                   17

<210> SEQ ID NO 12
<211> LENGTH: 17
<212> TYPE: DNA
<213> ORGANISM: Artificial Sequence
<220> FEATURE:
<223> OTHER INFORMATION: MDP1.5SF1-A, forward primer

<400> SEQUENCE: 12
cctgacccca tgccgaa                                                   17

<210> SEQ ID NO 13
<211> LENGTH: 19
<212> TYPE: DNA
<213> ORGANISM: Artificial Sequence
<220> FEATURE:
<223> OTHER INFORMATION: MDP1.6SF1-A, forward primer

<400> SEQUENCE: 13
agttagcgac agccgcagc                                                 19

<210> SEQ ID NO 14
```

```
<211> LENGTH: 19
<212> TYPE: DNA
<213> ORGANISM: Artificial Sequence
<220> FEATURE:
<223> OTHER INFORMATION: MDP1.7SF1-A, forward primer

<400> SEQUENCE: 14
atggctacgc agcggaaac                                                  19

<210> SEQ ID NO 15
<211> LENGTH: 22
<212> TYPE: DNA
<213> ORGANISM: Artificial Sequence
<220> FEATURE:
<223> OTHER INFORMATION: MDP1.8SF1-A, forward primer

<400> SEQUENCE: 15
gcggcatatg ttttacctcc tg                                              22

<210> SEQ ID NO 16
<211> LENGTH: 23
<212> TYPE: DNA
<213> ORGANISM: Artificial Sequence
<220> FEATURE:
<223> OTHER INFORMATION: MDP1.9SF1-A, forward primer

<400> SEQUENCE: 16
agctcgtaat tgttatccgc tca                                             23

<210> SEQ ID NO 17
<211> LENGTH: 19
<212> TYPE: DNA
<213> ORGANISM: Artificial Sequence
<220> FEATURE:
<223> OTHER INFORMATION: MDP1.10SF1-A, forward primer

<400> SEQUENCE: 17
caagcaaagt gacaggcgc                                                  19

<210> SEQ ID NO 18
<211> LENGTH: 22
<212> TYPE: DNA
<213> ORGANISM: Artificial Sequence
<220> FEATURE:
<223> OTHER INFORMATION: MDP1.11SF1-A, forward primer

<400> SEQUENCE: 18
ggcggtaata cggttatcca ca                                              22

<210> SEQ ID NO 19
<211> LENGTH: 22
<212> TYPE: DNA
<213> ORGANISM: Artificial Sequence
<220> FEATURE:
<223> OTHER INFORMATION: MDP1.12SF1-A, forward primer

<400> SEQUENCE: 19
tgcgccttat ccggtaacta tc                                              22

<210> SEQ ID NO 20
<211> LENGTH: 20
<212> TYPE: DNA
<213> ORGANISM: Artificial Sequence
<220> FEATURE:
<223> OTHER INFORMATION: MDP1.13SF1-A, forward primer

<400> SEQUENCE: 20
```

```
tttggtcat gagtcactgc                                                   20

<210> SEQ ID NO 21
<211> LENGTH: 20
<212> TYPE: DNA
<213> ORGANISM: Artificial Sequence
<220> FEATURE:
<223> OTHER INFORMATION: MDP1.14SF1-A, forward primer

<400> SEQUENCE: 21
ggaacgatgc cctcattcag                                                  20

<210> SEQ ID NO 22
<211> LENGTH: 23
<212> TYPE: DNA
<213> ORGANISM: Artificial Sequence
<220> FEATURE:
<223> OTHER INFORMATION: MDP1.15SF1-A, forward primer

<400> SEQUENCE: 22
ccagcggata gttaatgatc agc                                              23

<210> SEQ ID NO 23
<211> LENGTH: 20
<212> TYPE: DNA
<213> ORGANISM: Artificial Sequence
<220> FEATURE:
<223> OTHER INFORMATION: MDP1.16SF1-A, forward primer

<400> SEQUENCE: 23
ccggcatact ctgcgacatc                                                  20

<210> SEQ ID NO 24
<211> LENGTH: 20
<212> TYPE: DNA
<213> ORGANISM: Artificial Sequence
<220> FEATURE:
<223> OTHER INFORMATION: MDP1.17SR1-A, reverse primer

<400> SEQUENCE: 24
gatgtcgcag agtatgccgg                                                  20

<210> SEQ ID NO 25
<211> LENGTH: 23
<212> TYPE: DNA
<213> ORGANISM: Artificial Sequence
<220> FEATURE:
<223> OTHER INFORMATION: MDP1.18SR1-A, reverse primer

<400> SEQUENCE: 25
cattaactat ccgctggatg acc                                              23

<210> SEQ ID NO 26
<211> LENGTH: 18
<212> TYPE: DNA
<213> ORGANISM: Artificial Sequence
<220> FEATURE:
<223> OTHER INFORMATION: MDP1.19SR1-A, reverse primer

<400> SEQUENCE: 26
gccaacgatc agatggcg                                                    18

<210> SEQ ID NO 27
<211> LENGTH: 24
<212> TYPE: DNA
```

```
<213> ORGANISM: Artificial Sequence
<220> FEATURE:
<223> OTHER INFORMATION: MDP1.20SR1-A, reverse primer

<400> SEQUENCE: 27
tgaccaaaat cccttaacgt gagt                                              24

<210> SEQ ID NO 28
<211> LENGTH: 22
<212> TYPE: DNA
<213> ORGANISM: Artificial Sequence
<220> FEATURE:
<223> OTHER INFORMATION: MDP1.21SR1-A, reverse primer

<400> SEQUENCE: 28
gatagttacc ggataaggcg ca                                                22

<210> SEQ ID NO 29
<211> LENGTH: 21
<212> TYPE: DNA
<213> ORGANISM: Artificial Sequence
<220> FEATURE:
<223> OTHER INFORMATION: MDP1.22SR1-A, reverse primer

<400> SEQUENCE: 29
cctgcgttat ccctgattc t                                                  21

<210> SEQ ID NO 30
<211> LENGTH: 22
<212> TYPE: DNA
<213> ORGANISM: Artificial Sequence
<220> FEATURE:
<223> OTHER INFORMATION: MDP1.23SR1-A, reverse primer

<400> SEQUENCE: 30
aaacgacggc cagtcttaag ct                                                22

<210> SEQ ID NO 31
<211> LENGTH: 20
<212> TYPE: DNA
<213> ORGANISM: Artificial Sequence
<220> FEATURE:
<223> OTHER INFORMATION: MDP1.24SR1-A, reverse primer

<400> SEQUENCE: 31
aacgtaaaaa cccgcttcgg                                                   20

<210> SEQ ID NO 32
<211> LENGTH: 21
<212> TYPE: DNA
<213> ORGANISM: Artificial Sequence
<220> FEATURE:
<223> OTHER INFORMATION: MDP1.25SR1-A, reverse primer

<400> SEQUENCE: 32
cgcctgtcac tttgcttgat a                                                 21

<210> SEQ ID NO 33
<211> LENGTH: 23
<212> TYPE: DNA
<213> ORGANISM: Artificial Sequence
<220> FEATURE:
<223> OTHER INFORMATION: MDP1.26SR1-A, reverse primer

<400> SEQUENCE: 33
tgagcggata acaattacga gct                                               23
```

<210> SEQ ID NO 34
<211> LENGTH: 19
<212> TYPE: DNA
<213> ORGANISM: Artificial Sequence
<220> FEATURE:
<223> OTHER INFORMATION: MDP1.27SR1-A, reverse primer

<400> SEQUENCE: 34
ttgctcccgt aaagccctg                                              19

<210> SEQ ID NO 35
<211> LENGTH: 23
<212> TYPE: DNA
<213> ORGANISM: Artificial Sequence
<220> FEATURE:
<223> OTHER INFORMATION: MDP1.28SR1-A, reverse primer

<400> SEQUENCE: 35
cccgatctct attctgttca tcg                                         23

<210> SEQ ID NO 36
<211> LENGTH: 23
<212> TYPE: DNA
<213> ORGANISM: Artificial Sequence
<220> FEATURE:
<223> OTHER INFORMATION: MDP1.29SR1-A, reverse primer

<400> SEQUENCE: 36
tacggcgttt cacttctgag ttc                                         23

<210> SEQ ID NO 37
<211> LENGTH: 21
<212> TYPE: DNA
<213> ORGANISM: Artificial Sequence
<220> FEATURE:
<223> OTHER INFORMATION: MDP1.30SR1-A, reverse primer

<400> SEQUENCE: 37
ggtgcgacaa tctatcgctt g                                           21

<210> SEQ ID NO 38
<211> LENGTH: 19
<212> TYPE: DNA
<213> ORGANISM: Artificial Sequence
<220> FEATURE:
<223> OTHER INFORMATION: MDP1.31SR1-A, reverse primer

<400> SEQUENCE: 38
gatcgcgtat ttcgcctcg                                              19

<210> SEQ ID NO 39
<211> LENGTH: 21
<212> TYPE: DNA
<213> ORGANISM: Artificial Sequence
<220> FEATURE:
<223> OTHER INFORMATION: MDP1.32SR1-A, reverse primer

<400> SEQUENCE: 39
ctgcctcggt gagttttctc c                                           21

METHODS AND COMPOSITIONS OF HUMAN RECOMBINANT GROWTH AND DIFFERENTIATION FACTOR-5 (RHGDF-5) ISOLATED FROM INCLUSION BODIES

BACKGROUND

The present disclosure relates generally to a recombinant human growth and differentiation factor-5 (rhGDF-5) protein and, specifically to expression vector systems for increased production of rhGDF-5, host cells or cell lines for producing rhGDF-5, methods of producing rhGDF-5 using the host cells or cell lines and methods of enhancing production and protein expression of rhGDF-5 protein that are cost-effective, time-saving and manufacturing quality.

Biologic, a therapeutic product, can be made by genetically engineering living cells and requires a high level of precision and care and various factors for its manufacturing process to yield a consistent biologic product each time. For example, a biologic that is produced by recombinant host cells, either in prokaryotes or eukaryotes, can be influenced by (i) individual cell characteristics and (ii) the environment and nutrients provided during the manufacturing process. An example of a biologic is Growth and Differentiation Factor-5 (GDF-5).

GDF-5 belongs to the Bone Morphogenetic Protein (BMP) family, which itself is a subclass of the transforming growth factor-β superfamily of proteins. There are several variants and mutants of GDF-5 (GDF family members), some of which include the first isolated mouse GDF-5 (U.S. Pat. No. 5,801,014); MP52, a human form of GDF-5 (hGDF-5; (WO 95/04819)) or LAP-4 (Triantfilou et al., Nature Immunology 2, 338-345, 2001); cartilage-derived morphogenetic protein (CDMP)-1, an allelic protein variant of hGDF-5 (Chang, S. C. et al., J. Biol. Chem. 269(45):28227-34 (1994); WO 96/14335); rhGDF-5, a recombinant human form prepared from bacteria (EP 0955313); rhGDF-5-Ala83, a monomeric variant of rhGDF-5; BMP-14, a collective term for hGDF-5/CDMP-1 like proteins; SYNS2; Radotermin, the international non-proprietary name designated by the World Health Organization; HMW MP52's, high molecular weight protein variants of MP52; C465A, a monomeric version wherein the cysteine residue responsible for the intermolecular cross-link is substituted with alanine; also other active monomers and single amino acid substitution mutants including N445T, L441 P, R438L, and R438K.

The GDF-5 family members share common structural features including a carboxy terminal active domain and is characterized by a polybasic proteolytic processing site, which can be cleaved to release a mature protein containing seven conserved cysteine residues. The conserved pattern of cysteine residues creates 3 intra-molecular disulfide bonds and one inter-molecular disulfide bond. The active form can be either a disulfide-bonded homodimer of a single family member or a heterodimer of two different members (Massague et al., Ann. Rev. Cell Biol. 6:957 (1990); Sampath et al., J. Biol. Chem. 265:13198 (1990); Celeste et al., Proc. Natl. Acad. Sci. USA 87:9843-7 (1990); U.S. Pat. No. 5,011,691 and U.S. Pat. No. 5,266,683). The proper folding of the GDF-5 protein and formation of these disulfide bonds are essential to biological functioning, and misfolding leads to inactive aggregates and cleaved fragments.

GDF-5 is expressed in the developing central nervous system (O'Keeffe, G. et al., J. Neurocytol. 33(5):479-88 (2004) and has a role in skeletal and joint development (Buxton, P. et al., J. Bone Joint Surg. Am. 83-A, S1(Pt. 1):S23-30 (2001); Francis-West, P. et al., Development 126(6):1305-15 (1999); Francis-West, P. et al., Cell Tissue Res. 296(1):111-9 (1999)).

The GDF-5 family members are regulators of cell growth and differentiation in both embryonic and adult tissues. For example, GDF-5 may induce angiogenesis in the bone formation process (Yamashita, H. et al., Exp. Cell Res. 235(1): 218-226 (1997); CDMP-1 stimulates activity of articular chondrocytes thereby contributing to the integrity of the joint surface (Erlacher, L. et al., Arthritis Rheum. 41(2):263-73 (1998)). Changes in expression patterns of GDF-5 and its receptors are associated with human articular chondrocyte dedifferentiation (Schlegel, W. et al., J. Cell Mol. Med. 13(9B):3398-404 (2009)). As a growth factor, GDF-5 (CDMP) may stimulate proteoglycan production in the human degenerate intervertebral disc (Le Maitre, C. L. et al., Arthritis Res. Ther. 11(5):R137 (2009)). It may increase the survival of neurons that respond to a dopamine neurotransmitter and can be a potential therapeutic molecule associated with Parkinson's disease. (Sullivan and O'Keeffe, J. Anat. 207(3):219-26 (2005)). When rhGDF-5 was delivered on beta-tricalcium phosphate, an effective encouragement of periodontal tissue regeneration in non-human primates was observed. In tissues critical for periodontal repair (e.g. alveolar bone, cementum and periodontal ligament), rhGDF-5 treatment on these tissues showed evidence of regeneration and the response was found to be dose-dependent (Emerton, K. B. et al., J. Dental Res. 90(12):1416-21 (2011). Based on this finding and other similar reports, a biologic such as GDF-5 may offer new approaches or options to regenerate bone during dental implant placement and may save a tooth in patients who are at risk for tooth loss due to periodontal disease.

GDF-5 gene mutations can be associated with the following health conditions, e.g., acromesomelic chrondrodysplasia Grebe type (AMDG; (Thomas, J. T. et al., Nat. Genet. 1:58-64 (1997);), Hunter-Thompson type (AMDH; (Thomas, J. T. et al., Nat. Genet. 3:315-7 (1996)); brachydactyly type C (BDC; Francis-West, P. H. et al., Development, 126(6):1305-15 (1999), Everman, D. B. et al., Am. J. Med. Genet., 112(3): 291-6 (2002), Schwabe, G. C. et al., Am. J. Med. Genet. A. 124A(4):356-63 (2004)); DuPan syndrome (DPS), which is also known as fibular hypoplasia and complex brachydactyly (Faiyaz-Ul-Hague, M. et al., Clin. Genet. 61(6):454-8 (2002)); Mohr-Wriedt brachydactyly type A2 (Kjaer, K. W. et al., J. Med. Genet. 43(3):225-31 (2006)); multiple synostoses syndrome type 2 (SYNS2; Dawson, K. et al., Am. J. Human Genet. 78(4):708-12 (2006), Schwaerzer, G. K. et al., J. Bone Miner. Res. 27(2):429-42 (2012)); semidominant brachydactyly A1 (BA1; Byrnes, A. M. et al., Hum. Mutat. 31 (10): 1155-62 (2010)); symphalangism (SYM1; Yang, W. et al., J. Hum. Genet. 53(4):368-74 (2008)) or brachydactyly type A2 (BDA2; Seemann, P. et al., J. Clin. Invest. 115(9):2373-81 (2005), Plöger, F. et al., Hum. Mol. Genet. 53(4):368-74 (2008)); susceptibility to osteoarthritis type 5 (OS5; Masuya, H. et al., Hum. Molec. Genet. 16:2366-75 (2007), Miyamoto, Y. et al., Nature Genet. 39:529-53 (2007)); knee osteoarthritis in Thai ethnic population (Tawonsawatruk, T. et al., J. Orthop. Surg. Res. 6:47 (2011)). GDF5 gene variants have been associated with hand, knee osteoarthritis and fracture risk in elderly women, which replicates the previous association between GDF5 variation and height. (Vaes, R. B. et al., Ann Rheum. Dis. 68(11):1754-60 (2009)). All of these associations confirmed that the GDF-5 gene product may play a role in skeletal development.

Expression of GDF-5-related proteins using recombinant DNA techniques has been done and their purification and production for industrial scale have also been explored. See for example, Hötten, U.S. Pat. No. 6,764,994; Makishima, U.S. Pat. No. 7,235,527; Ehringer, U.S. Pat. No. 8,187,837).

Both Hötten and Makishima described (1) a complete DNA nucleotide sequence that codes for the TGF-β protein MP-52 and the complete amino acid sequence of MP52; and (2) a composition containing a pharmaceutically active amount of the MP-52 for wound healing and tissue regeneration, treating cartilage and bone diseases and dental implants. According to Makashina, isolation of pure MP-52 at least with the mature region from the mixture was difficult (Makashina, column 1, lines 59-61). To overcome this obstacle, Makashina constructed a DNA plasmid wherein a codon encoding methionine was linked to the DNA sequence that encodes for a 119-amino acid residue protein (MP-52) and wherein the N-terminal alanine of the mature MP-52 protein (120-amino acid residue) was eliminated. Ehringer, on the other hand, described an advanced method for the efficient prokaryotic production and purification of GDF-5 related proteins that resulted in better protein yield, high product purity and improved industrial applicability. Problems encountered during the purification and refolding of the GDF-5-related proteins in large scale were disclosed and addressed.

The use of prokaryotic expression vectors such as bacterial plasmids for expressing preventive or therapeutic peptides (biologics) is very critical and beneficial not only for biochemical research and biotechnology but even more so for medical therapy. Such use is the basis of many biologics manufacturing processes. High-cell density (HCD) fermentation methods that employ these processes offer many advantages over traditional methods in that the final product concentrations are higher, downtime and water usage are reduced, and overall productivity is improved resulting in lower set-up and operating costs.

The recombinant protein and plasmid DNA production typically involves: (1) bacterial propagation and fermentation production, wherein a plasmid encoding a gene of interest is transformed into a bacterial cell, typically Escherichia coli (E. coli), propagated to make master and working cell banks, and further grown in a bioreactor (e.g., fermentor) to make production cells that contain high yields of the plasmid; and (2) purification and formulation stability, wherein the production cells are lysed and plasmid DNA carrying the gene of interest is purified by a plurality of purification methods and formulated for delivery. Expression is particularly higher if the gene of interest is codon optimized to match that of the target organism, which leads to improved gene function and increased protein expression, which ultimately leads to cost-effectiveness of mass producing the recombinant protein.

Plasmid fermentation processes for plasmid production should be optimized to retain a high percentage of supercoiled plasmid. Other plasmid forms are difficult to eliminate during purification and their presence are undesirable. Fermentation media and processes needs to be optimized for plasmid yield, plasmid quality and compatibility of the resultant cells for harvest and lysis. There are about three fermentation processes that can be utilized to initiate production, namely: batch, batch-fed or continuous fermentation processes. For a large scale production, a batch fermentation that generally yields about 10-20 mg/L of plasmid DNA has its limitations such as uncontrolled growth rates and waste product accumulation (e.g., production of reduced carbon metabolites such as acetates, lactates and formates) that ultimately would lead to inhibition of bacterial growth. To prevent these issues from occurring and to increase plasmid yield, fed-batch or continuous high cell density fermentation can be a better option. Continuous fermentation processes are more conducive to the production of large amounts of a single product but sterility remains an issue. Fed-batch fermentation begins with a short batch fermentation and is proceeded by the addition of media at a defined rate. It is more flexible and consistent than the batch method and allows for simple optimization of fermentation profiles for each plasmid DNA product. When employing a defined growth rate strategy as a form of feed strategy, a feed media is added at rates that are determined based on a pre-established growth profile, wherein the feed is triggered by an initial DO2 spike (caused by the exhaustion of initial bolus of glucose in the media). Peterson, M. and Brune, M., in BioPharm International Supplements entitled: "Maximizing Yields of Plasmid DNA Processes," Jun. 2, 2008.

Chemically-defined (minimal) media contain known quantities of ingredients added to purified water. The absence of animal-derived components in chemically-defined media may be more desirable from a regulatory standpoint due to concerns over BSE/TSE (spongiform encephalopathy/transmissible spongiform encephalopathy). They have reproducibility (their components have known chemical structures that can allow consistent performance of cells in the medium), greater simplicity of both downstream processing and the analysis of product and greater control of feeding strategy when carbon sources are known.

Complex media, on the other hand, are digests of food and agriculture by-products (i.e. protein hydrolysate and yeast extract). They can provide a majority of needed nutrients to host cell (e.g., Escherichia coli) fermentation. They may produce high yields at lower costs (thus, more cost-effective) and less control over individual components and possibly vary from lot-to-lot.

Semi-defined media contain small concentrations of complex ingredients usually from about 0.05 to about 0.5% added to a chemically defined media. Semi-defined media can maximize performance while minimizing downstream processing issues. Small amount of complex material may provide enough nutrients to enhance growth of microorganisms without interfering with recovery or analysis.

Given the role of GDF-5 in cell growth and differentiation, in particular, skeletal and joint development and bone regeneration, there is a critical need for a therapeutic rhGDF-5 biologic that can be manufactured in large scale processes. There is an urgent need for improving the manufacturing process of rhGDF-5 that can be cost-effective, time-saving and manufacturing quality.

SUMMARY

The present disclosure includes methods and compositions for the production of rhGDF-5 using the T5 or Trc promoter in the production of rhGDF-5 for therapeutic applications. The rh-GDF-5 can be easily produced in large scale quantities in a cost-effective and time-saving manner.

In various embodiments, there is a method provided for isolating recombinant GDF-5 protein from an inclusion body of a cell. The method comprises disrupting the cell via lysis or homogenization such that a pGDF-5 or a pGDF-5-Trc-transformed cell releases the inclusion body of rhGDF-5 protein and recovering the GDF-5 protein from the inclusion body comprising an expression vector having a T5 or a Trc promoter operatively linked to a polynucleotide sequence that encodes a GDF-5 protein by contacting the GDF-5 protein with a substrate.

In various embodiments, there is a method provided for isolating recombinant GDF-5 protein from an inclusion body of a prokaryotic cell. The method comprises disrupting the prokaryotic cell via lysis or homogenization such that a pGDF-5 or a pGDF-5-Trc-transformed cell releases the inclusion body of rhGDF-5 protein and recovering the GDF-5 protein from the inclusion body comprising an expression vector having a T5 or a Trc promoter operatively linked to a polynucleotide sequence that encodes a GDF-5 protein by contacting the GDF-5 protein with a substrate.

In various embodiments, a host cell line is provided. The cell line comprises an inclusion body comprising an isolated GDF-5 protein, wherein the host cell includes an expression vector which comprises a polynucleotide encoding for an rhGDF-5 protein under the control of a T5 or Trc promoter.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 1C shows a protein alignment of the theoretical amino acid sequence encoded by pGDF5-Trc and that of a commercially-known rhGDF-5 protein, as set forth in the Sequence Listing as SEQ ID NOs: 4 and 5, respectively.

FIGS. 3A and 3B are Western blots showing the absence and presence of GDF-5 protein in the supernatant and pellet fractions of selected pGDF5-Trc-transformed clones, respectively.

FIG. 3C shows the lanes and samples that correspond to the Western blots of FIGS. 3A and 3B.

FIG. 7 is an exemplary formulation of a high cell density media according to the embodiment of the present disclosure.

FIGS. 8A, 8B and 8C show the enhancing effects of sodium molybdate, magnesium sulfate, heptahydrate and sodium chloride on rhGDF-5 expression when these three components were added to Media 1, which was optimized based on its improved response to rhGDF-5 expression in the cultured pGDF5-Trc-transformed host cells. Data obtained were evaluated using statistical software.

FIGS. 9A and 9B show an increase of rhGDF-5 expression by the addition of yeast extract and magnesium sulfate into Media 2 (optimized based on its improved response to rhGDF-5 expression) but the addition of sodium molybdate decreased rhGDF-5 expression in pGDF5-Trc-transformed host cells. Data obtained were evaluated using statistical software.

FIGS. 9C and 9D show biomass optimization by the addition of yeast extract while negatively affected by the addition of sodium chloride and MOPS when these three components were added to Media 3, which was optimized based on its improved response to biomass yield in the growth of pGDF5-Trc-transformed host cells. Data obtained were evaluated using statistical software.

FIGS. 9E and 9F show the results for the optimization of the culture media.

FIGS. 11A-C are Coomassie brilliant blue-stained gels showing the level of GDF-5 protein production and expression of pGDF5Trc-transformed HMS174 cells when grown under (a) pH 6.5 (condition A); (b) pH 7.1 (condition B); and (c) pH 6.8 at low oxygen (condition C), respectively.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present disclosure are approximations, the numerical are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

It is noted that, as used in this specification and the appended claims, the singular forms "a," "an," and "the" include plural referents unless expressly and unequivocally limited to one referent.

For the purposes of this application the term "GDF-5" is meant to include all variants and mutants of the GDF-5 protein, and rhGDF-5 is an exemplary member having 125 amino acids as set forth in the Sequence Listing as SEQ ID NO:4.

Figure 1A:
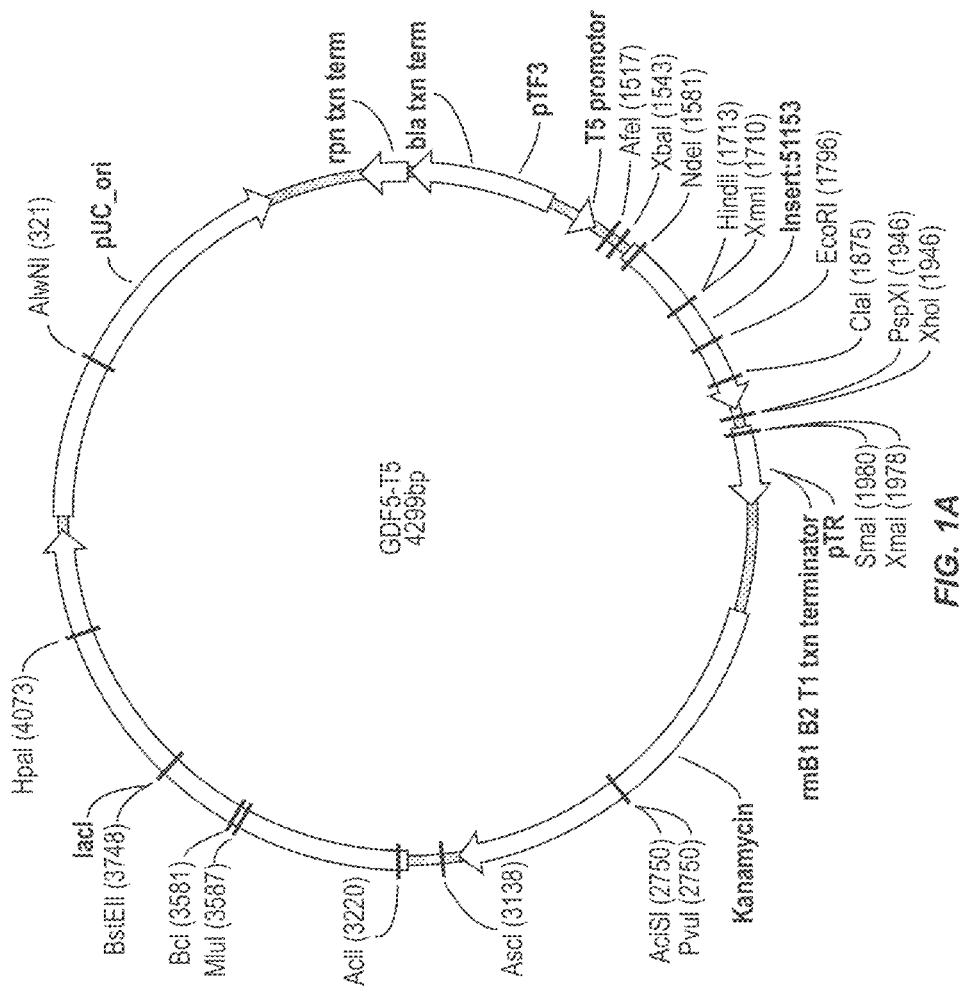
FIGS. 1A and 1B are plasmid maps of pGDF5-T5 and pGDF5-Trc expression vectors, respectively.

The term "cysteine-knot domain" refers to a conserved cysteine-rich amino acid region that is present in the mature parts of TGF-β superfamily proteins, such as i.e. human GDF-5 and forms a three-dimensional protein structure known as cysteine-knot. It has been shown that the cysteine-knot domain alone is sufficient for the biological function of the protein (Schreuder et al., Biochem. Biophys. Res. Commun. 329:1076-86 (2005)). Consensus sequences for cysteine-knot domains are well known in the state of the art. The cysteine-knot-domain of a protein starts with the first cysteine residue participating in the cysteine-knot of the respective protein and ends with the residue which follows the last cysteine participating in the cysteine-knot of the respective protein. For example, the cysteine-knot domain of the human GDF-5 precursor protein consists of the amino acids 24-125 (see the underlined region of the amino acid sequence of SEQ ID NO:4 encoded by pGDF5-Trc as shown in FIG. 1C).

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well-known molecular biological procedures. A "recombinant DNA molecule" is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

A "polynucleotide sequence" or "nucleotide sequence" or "nucleic acid sequence," as used interchangeably herein, is a polymer of nucleotides, including an oligonucleotide, a DNA, and an RNA, a nucleic acid or a character string representing a nucleotide polymer, depending on context. From any specified polynucleotide sequence, either the given nucleic acid or the complementary polynucleotide sequence can be determined. Included is DNA or RNA of genomic or synthetic origin which may be single- or double-stranded and represent the sense or anti-sense strand.

The term "oligonucleotide" as used herein includes naturally occurring, and modified nucleotides linked together by naturally occurring and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or to 40 bases in length. Oligonucleotides are usually single stranded, e.g. for primers and probes; although oligonucleotides may be double stranded, e.g. for use in the construction of a gene mutant. Oligonucleotides of the present disclosure can be either sense or anti-sense oligonucleotides.

As used herein, the terms "nucleic acid molecule encoding," "DNA sequence encoding" and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

As used herein the term "coding region" when used in reference to a structural gene refers to the nucleotide sequences which encode the amino acids found in the nascent polypeptide as a result of translation of an mRNA molecule.

Recombinant DNA-mediated protein expression techniques are applicable to the making of the rhGDF-5 protein. Briefly, a recombinant DNA molecule or construct (pGDF5-T5 or pGDF5-Trc, the polynucleotide sequences of which are set forth in the Sequence Listing as SEQ ID NOS: 2 and 3, respectively), coding for the gene of interest (GDF-5, the polynucleotide sequence as set forth in Sequence Listing as SEQ ID NO:1) is prepared. Methods of preparing such DNA molecules are well known in the art. For instance, sequences encoding the gene of interest (e.g. rhGDF-5 or GDF-5 (SEQ ID NO: 1)) can be excised from DNA using suitable restriction enzymes. Any of a large number of available and well-known host cells may be used in the practice of this present disclosure. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all hosts may be equally effective for the expression of a particular DNA sequence. Within these general guidelines, useful microbial host cells in culture include bacteria such as *Escherichia coli* sp. Modifications can be made at the DNA level, as well. For example, the GDF-5 encoding DNA sequence (SEQ ID NO: 1) may be changed to codons more compatible with the chosen host cell. For *E. coli*, optimized codons are known in the art. Codons can be substituted to eliminate restriction sites or to include silent restriction sites, which may aid in processing of the DNA in the selected host cell. The transformed bacterial host cell line or cell strain is then cultured and purified. Host cells or strains may be cultured under conventional fermentation conditions so that the desired compounds are expressed. Such fermentation conditions are well known in the art.

The region of the vector to which the gene of interest is cloned is referred to herein as an "insertion site." Preferably, the gene of interest is rhGDF-5 or GDF-5, designated in the Sequence Listing as SEQ ID NO: 1.

In one embodiment, the vector comprises an Nde1 restriction site for restriction enzyme analysis purposes.

The term "expression vector" according to the embodiment of the present disclosure refers to a vehicle for introducing a gene of interest into a host cell to express the gene or a recombinant DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site and possibly other sequences. Expression vectors or vectors according to the embodiment of the present disclosure include plasmid vectors.

In one embodiment, the expression vectors of the present disclosure may include regulatory promoters, examples of which may include but are not limited to, T5, T7 and Trc promoters. The regulatory promoters of the present disclosure can be induced by isopropyl-β-D-thiogalactoside (IPTG).

The expression vectors of the present disclosure, which is provided for inducing high expression of a gene of interest (GDF-5 (SEQ ID NO:1)) in the host cells, may preferably further include a resistance gene for host cells, which is used as a selectable marker for permanent expression of the gene in the host cells. Non-limiting examples of such resistance genes for animal cells include those commonly used in the art, such as ampicillin-, neomycin-, kanamycin-, zeomycin- and hygromycin-resistant genes. A resistance gene, according to the embodiment of the present disclosure, is the Kanamycin-resistant (Kan$^r$ gene).

According to one embodiment of the present disclosure, the term "host cell" is used to refer to a cell which has been transformed, or is capable of being transformed with a nucleic acid sequence and then of expressing a selected gene of interest (GDF-5, SEQ ID NO:1). Thus, a host cell, as used herein, is also a transformed cell line (or strain) or a transformant.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "operably linked" refers to a functional linkage between an expression control sequence and a second nucleic acid sequence, wherein the expression control sequence directs transcription of the nucleic acid corresponding to the second sequence.

A host cell "engineered to overexpress" a protein (or a nucleic acid encoding such protein) is a host cell, including a descendant thereof, that has been altered in such a way that higher levels of such protein are expressed than normal, compared to the unaltered host cell. Thus, included within this category are expression of proteins foreign to the host cell, proteins not naturally expressed by the host cell, or proteins naturally expressed by the host cell at relatively low levels that increase after alteration of the host cell.

In a preferred aspect, the recombinant protein of interest (rhGDF-5 designated in the Sequence Listing as SEQ ID NO: 4) is expressed in the prokaryotic host cells, such as, for example *E. coli* host cells. Examples of prokaryotic host cell strains include, but are not limited to DH10β, STBL2, HMS174 and recA.

The term "isolated nucleic acid" refers to a nucleic acid of the present disclosure that is free from at least one contaminating nucleic acid with which it is naturally associated. A "nucleic acid" refers to a DNA or RNA sequence, optionally including artificial bases or base analogs.

The term "identity" (or "percent identical") is a measure of the percent of identical matches between the smaller of two or more sequences with gap alignments (if any) addressed by a particular mathematical model or computer program (i.e., "algorithms"). The term "similarity" is a related concept but, in contrast to "identity", includes both identical matches and conservative substitution matches. Identity and similarity of related nucleic acid molecules and polypeptides can be readily calculated by known methods. Preferred methods to determine identity and/or similarity are designed to give the largest match between the sequences tested. Methods to determine identity and similarity are described in publicly available computer programs. Exemplary computer program methods to determine identity and similarity between two sequences include, but are not limited to, the GCG program package, including GAP (Devereux et al., Nucl. Acids. Res. 12: 387, 1984; Genetics Computer Group, University of Wisconsin, Madison, Wis.), BLASTP, BLASTN, and FASTA (Altschul et al., J. Mol. Biol. 215:403-410, 1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith-Waterman algorithm may also be used to determine identity. Preferred parameters for a polypeptide sequence comparison include the following: Algorithm: Needleman et al., J. Mol. Biol. 48: 443-53 (1970); Comparison matrix: BLOSUM 62 from Henikoff et al., Proc. Natl. Acad. Sci. USA 89:10915-19 (1992); Gap Penalty: 12, Gap Length Penalty: 4; Threshold of Similarity: 0. The GAP program is useful with the above parameters (along with no penalty for end gaps). Preferred parameters for nucleic acid molecule sequence comparisons include the following: Algorithm: Needleman et al., J. Mol. Biol., 48:443-53 (1970); Comparison matrix: matches=+10, mismatch=0, Gap Penalty: 50, Gap Length Penalty: 3. The GAP program is also useful with the above parameters. Other exemplary algorithms, gap opening penalties, gap extension penalties, comparison matrices, thresholds of similarity, etc. may be used by those of skill in the art.

The phrase "stringent hybridization conditions" refers to conditions under which a probe will hybridize to its target subsequence, typically in a complex mixture of nucleic acid, but to no other sequences. Hybridization stringency is principally determined by temperature, ionic strength, and the concentration of denaturing agents such as formamide. Examples of "highly stringent conditions" for hybridization and washing are 0.015M sodium chloride, 0.0015M sodium citrate at 65-68° C. or 0.015M sodium chloride, 0.0015M sodium citrate, and 50% formamide at 42° C. See Sambrook, Fritsch & Maniatis, Molecular Cloning: A Laboratory Manual, 2nd Ed., Cold Spring Harbor Laboratory, (Cold Spring Harbor, N.Y. 1989); and Anderson et al., Nucleic Acid Hybridization: Hybridization: a practical approach, Ch. 4, IRL Press Limited (Oxford, England) (1999). Examples of typical "moderately stringent" conditions are 0.015M sodium chloride, 0.0015M sodium citrate at 50-65° C. or 0.015M sodium chloride, 0.0015M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

The nucleotide and amino acid sequences of pGDF5-T5 and pGDF5-Trc are set forth in SEQ ID NOS: 2 and 3 and SEQ ID NO: 4, respectively.

The term "rhGDF-5 or GDF-5" as used herein refers to human growth and differentiation factor-5 (the polypeptide of SEQ ID NO:4 encoded by the polynucleotide of SEQ. ID NO: 1) thereof, or a biologically active fragment, variant, analog, or derivative of the human GDF-5 protein. Exemplary analogs retain 65% or higher amino acid identity to the parent sequence, or 70%, 75%, 80%, 85%, 90%, 91%, 92%, 93%, 94%, 95%, 96%, 97%, 98%, or 99% or higher identity.

As used herein, the term "rhGDF-5 or GDF-5 (pGDF5-T5 or pGDF5-Trc nucleic acid" or "rhGDF-5 or GDF-5 (pGDF5-T5 or pGDF5-Trc) polynucleotide" refers to a nucleic acid that encodes a polypeptide having an amino acid sequence as set forth in SEQ ID NO:4, including a nucleotide sequence as set forth in SEQ ID NO: 1, or nucleic acids comprising nucleotide sequences that are at least about 65%, 70%, 75%, 80%, 85%, 90%, 95%, 96%, 97%, 98%, 99% or 100% identical thereto, or nucleic acids which hybridize under moderately or highly stringent conditions as defined herein with the complement of SEQ ID NO: 1 or any other orthologs of the nucleotide sequence of SEQ ID NO: 1.

The terms "polypeptide" and "protein" are used interchangeably herein.

Overexpression, as described herein, encompasses activating (or causing to be expressed) a gene which is normally silent (unexpressed) in the host cell as obtained, as well as increasing the expression of a gene which is not expressed at physiologically significant levels in the cell as obtained.

The present disclosure includes methods and compositions for the production of rhGDF-5 using the T5 or Trc promoter in the production of rhGDF-5 for therapeutic applications. The rh-GDF-5 can be easily produced in large scale quantities in cost-effective, and time-saving manner.

According to the embodiment of the present disclosure, the term "isolated protein" comprises rhGDF-5 or GDF5 protein. In one embodiment, the protein comprises rhGDF-5 or GDF5 having the amino acid sequence set forth in SEQ ID NO:4 and variants and derivatives of this protein, which retain the activity of the polypeptide of SEQ ID NO: 4. In one embodiment, the protein comprises a polypeptide having at least about 80% identity, at least about 85% identity, at least about 90% identity, at least about 95% identity, at least about 98% identity, or at least about 99% identity to the amino acid sequence set forth in SEQ ID NO: 4.

Stable production of proteins, including biologics, can be accomplished by transfecting host cells with vectors containing DNA that encodes the protein. Maintenance of the vector in the cell line can be achieved through a variety of means With the evolving importance of therapeutic proteins, i.e., biologics, efforts must be made to optimize protein production, while improving efficiency of the overall production process. Thus, improvements in efficiency must be weighed against the protein production capacity of the vector. There is a need for better expression systems that provide efficient cloning options, as well as high levels of the desired protein product. It would be advantageous to decrease the number of cloning steps involved in the production of biologics to improve time requirements and minimize cost. It would also be advantageous to provide vectors that provide adequate protein production for both small and large scale cell cultures.

After the expression vector is introduced into the cells, the transfected cells are cultured under conditions favoring expression of the protein, which may be recovered from the culture using standard techniques identified below by contacting the protein with a substrate (e.g., resin, glass, plastic, cellulose, etc.) that is capable of immobilizing the protein.

The substrate comprises at least one surface on which to capture the GDF-5 protein. The substrate may comprise a ceramic substance, a glass, a metal, a crystalline material, a plastic, a polymer or co-polymer, any combinations thereof, or a coating of one material on another. Such substrates include for example, but are not limited to, (semi) noble metals such as gold or silver; glass materials such as soda-lime glass, pyrex glass, vycor glass, quartz glass; resins, cellulose, metallic or non-metallic oxides; silicon, monoammonium phosphate, and other such crystalline materials; transition metals; plastics or polymers, including dendritic polymers, such as poly(vinyl chloride), poly(vinyl alcohol), poly(methyl methacrylate), poly(vinyl acetate-maleic anhydride), poly(dimethylsiloxane)monomethacrylate, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

The substrate may take a variety of configurations ranging from simple to complex, depending on its intended use. Thus, the substrate could have an overall slide or plate configuration, such as a rectangular or disc configuration or be part of a column.

Proteins (e.g., rh-GDF-5) and/or fragments thereof can be purified from any suitable expression system. If desired, the protein may be purified to substantial purity by standard techniques, including selective precipitation with such substances as ammonium sulfate; column chromatography, immunopurification methods, and others (see, e.g., Scopes, Protein Purification: Principles and Practice (1982); and U.S. Pat. No. 4,673,641. However, in the practice, purified or partially purified proteins are not required for either treatment with a modifying agent or generation of antibodies. If purification of the a conformationally trapped protein is desired, the presence of the modifying agent may be used to aid in the purification by allowing a skilled artisan to follow the location of the conformationally trapped protein during various purification steps such as those described below.

Recombinant proteins (e.g., rh-GDF-5) can be expressed by transformed bacteria in large amounts, typically after promoter induction; but expression can be constitutive. Promoter induction with a T5 or a Trc promoter is one example of an inducible promoter system. Bacteria are grown. Fresh or frozen bacteria cells are used for isolation of protein. Proteins (e.g., rh-GDF-5) expressed in bacteria may form insoluble aggregates ("inclusion bodies"). Several protocols are suitable for purification of the expressed proteins from inclusion bodies. For example, purification of inclusion bodies typically involves the extraction, separation and/or purification of inclusion bodies by disruption of bacterial cells. The cell suspension can be lysed using 2-3 passages through a French Press; homogenized using, for example, a Polytron (Brinkman Instruments); disrupted enzymatically, e.g., by using lysozyme; or sonicated on ice. Alternate methods of lysing bacteria are apparent to those of skill in the art (see, Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

If necessary, the inclusion bodies are solubilized, and the lysed cell suspension is typically centrifuged and/or filtered to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. One of skill in the art will recognize that optimal conditions for renaturation must be chosen for each protein. For example, if a protein is soluble only at low pH, renaturation can be done at low pH. Renaturation conditions can thus be adjusted for proteins with different solubility characteristics i.e., proteins that are soluble at neutral pH can be renatured at neutral pH.

The expressed protein (e.g., rh-GDF-5) is separated from other bacterial proteins by standard separation techniques, such as for example, solubility fractionation, size differential filtration, column chromatography, or the like. Solubility fractionation involves an initial salt fractionation can separate many of the unwanted host cell proteins (or proteins derived from the cell culture media) from the recombinant protein of interest. In some embodiments, ammonium sulfate can be used. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size differential filtration involves using the molecular weight of a given protein to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column chromatography involves separating a protein from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). In one embodiment, the column comprises a resin that binds the GDF-5 protein in order to isolate the rh-GDF-5 protein. The protein can be washed from the resin and washed with a buffer to refold the GDF-5 protein.

In some embodiments, the rh-GDF-5 can be isolated on the substrate in different conformational states. A modifying agent can be contacted with a protein of interest to fix the protein in a specific conformational state. The interaction of the modifying agent may be covalent or non-covalent and may be reversible or essentially irreversible. Functional groups on proteins that may serve as sites for attachment of modifying agents include sulfhydryl, amino, and carboxyl groups found on the side chains of various amino acids. Furthermore, other features of a protein such as charge, hydrophobicity, or hydrogen bonding potential, among others, may serve as a point of association between a modifying agent and a protein. Examples of trapping of conformational states using modifying agents such as those which react with sulfhydryl groups may be found in: Erlanson et al., Annual Review of Biophys. Biomol. Struct., 33:199-223 (2004), Erlanson, et al., Curr. Opin. Chem. Biol., 8: 399-406 (2004), Erlanson et al., J. Med. Chem., 47: 3463-3482 (2004), Hardy et al., Proc. Nat'l. Acd. Sci., 34: 12461-12466 (2004); Buck and Wells, Proc. Nat'l. Acd. Sci., 102: 2719-2724 (2005); Scheer et al., Proc. Nat'l. Acd. Sci., 103: 7595-7600 (2006), which are incorporated by reference in their entirety.

Antibodies can be used to isolate the rh-GDF-5 in different conformational states. Methods of producing polyclonal and monoclonal antibodies that react specifically with proteins are known to those of skill in the art and can be readily adapted to generate conformation specific antibodies by using the conformationally trapped proteins described above as antigens (see, e.g., Coligan, Current Protocols in Immunology (1991); Harlow & Lane, supra; Goding, Monoclonal Antibodies: Principles and Practice (2d ed. 1986); and Kohler & Milstein, Nature 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341: 544-546 (1989)).

Methods of production of polyclonal antibodies are known to those of skill in the art. An inbred strain of mice (e.g., BALB/C mice) or rabbits is immunized with the protein (i e., immunogen) using a standard adjuvant, such as Freund's adjuvant, and a standard immunization protocol. The animal's immune response to the immunogen preparation is monitored by taking test bleeds and determining the titer of reactivity to the protein. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., Science 246:1275-1281 (1989).

Monoclonal antibodies and polyclonal sera are collected and titered against the immunogen protein (e.g., GDF-5) in an immunoassay, for example, a solid phase immunoassay with the immunogen immobilized on a solid support. Typically, polyclonal antisera with a titer of $10^4$ or greater are selected and tested for their cross reactivity against non-conformationally trapped proteins or proteins trapped in a conformation different from that used to raise the antibody. Specific polyclonal antisera and monoclonal antibodies will usually bind with a Kd of at least about 0.1 mM, more usually at least about 1 µM, preferably at least about 0.1 µM or better, and most preferably, 0.01 µM or better.

Once antibodies specific to a particular conformational state are available, the antibodies can be labeled with a suitable label (e.g., dye, fluorophore, tage, etc.) to identify the particular conformational state of the GDF-5 protein or to identify the GDF-5 protein if needed. The antibodies used to identify the GDF-5 protein may optionally be covalently or non-covalently linked to a detectable label. Detectable labels suitable for such use include any composition detectable by spectroscopic, photochemical, biochemical, immunochemical, electrical, optical or chemical means. Useful include magnetic beads (e.g. DYNABEADS), fluorescent dyes (e.g., Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 dyes, fluorescein isothiocyanate, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Conformation specific antibodies may be used in virtually any assay format that employs antibodies to detect antigens. Design of the immunoassays is subject to a great deal of variation, and many formats are known in the art. Protocols may, for example, use solid supports, or immunoprecipitation. Many assays involve the use of labeled antibody or polypeptide; the labels may be, for example, enzymatic, fluorescent, chemiluminescent, radioactive, or dye molecules, as discussed in detail above. Assays which amplify the signals from the immune complex are also known; examples of which are assays which utilize biotin and avidin, and enzyme-labeled and mediated immunoassays, such as ELISA assays.

In one embodiment, the expressed recombinant rhGDF-5 protein, according to the embodiment of the present disclosure, can be collected from pGDF5-T5 or pGDF5-Trc transformed host cell lysates (from strains DH10β, STBL2, HMS174 or RecA). The supernatant (soluble fraction) and pellet (insoluble fraction containing inclusion bodies) can be separated by centrifugation. The pellet may then be collected and disrupted or homogenized to release the inclusion bodies from the bacterial cells. Host cell disruption or homogenization may be performed using well known techniques including, but not limited to, enzymatic cell disruption, sonication, dounce homogenization or high pressure release disruption. In one embodiment, the techniques disclosed are used to disrupt the pGDF5-T5- or pGDF5-Trc-transformed *E. coli* cells to release the inclusion bodies of rhGDF-5 protein.

In one embodiment, after cell disruption, the inclusion bodies may then be subjected to solubilization using suitable denaturing agents known in the art. The denaturing agents may be urea or guanidine hydrochloride. The recombinant rhGDF-5 protein can be recovered and purified from the resulting solution by any of a number well known in the art, including but are not limited to, using ion-exchange chromatography, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. Once purified, partially or to homogeneity, as desired, the rhGDF-5 proteins are optionally used for a wide variety of utilities, including but not limited to, as assay components, therapeutics (biologics), prophylaxis, diagnostics, research reagents, and/or as immunogens for antibody production.

In addition to other references noted herein, a variety of purification/protein folding methods are well known in the art, including, but not limited to, those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein.

As used herein, the term "exponential growth" refers to that portion of the cellular growth cycle between the lag phase and the stationary phase when cells are doubling at a logarithmic rate. The term "exponential growth" is also meant to encompass the late lag phase (i.e., the early stationary phase) which occurs between the logarithmic growth phase and stationary phase, when the cell growth rate is slowing, and therefor encompasses an extended exponential growth phase. Therefore, "stationary phase" refers to horizontal growth, i.e., when the cells have essentially stopped dividing and have reached a quiescent stage with respect to cell doubling.

As in conventional fermentation processes, it is usually desirable to obtain as high a rate of cell growth in as high a density of bacterial cell culture as possible, to maximize the amount of bacterial biomass produced per unit of time. "Biomass," as utilized herein and without alteration from its conventional meaning, refers to the mass and/or accumulating mass of host bacterial cells or transforming bacteria cells resulting from the cultivation of such cells using a variety of techniques, e.g., cultivating such cells in defined or semi-defined media containing additional ingredients that may enhance or increase bacterial growth rate or biomass.

According to the embodiment of the present disclosure, fermentation processes have been developed to maximize the yield of pGDF5-T5 and pGDF5-Trc DNAs from large scale cultures of transformed host cells and to optimize recombinant hGDF-5 protein production. The fermentation processes includes optimizing the plasmid yield such that the supply of metabolites essential for growth is adequate to permit growth to a high biomass, but is not in excess so as to inhibit such growth.

According to one embodiment, host cells transformed with an expression vector that includes a pGDF5-Trc or pGDF5-T5 DNA are cultured in a high cell density medium that are modified based on its response to protein expression and biomass yield. For example, a defined media may additionally include ingredients such as sodium molybdate (ranges from about 5 to about 10 mg/L), magnesium sulfate heptahydrate (ranges from about 2 to about 6 mM), sodium chloride (ranges from 0 to about 4 g/L), EDTA (ranges from 0 to about 400 mg/L), MOPS (ranges from 0 to about 100 mM), amino acid supplement including L-methionine (ranges from 0 to about 10 ml/L) and vitamin supplement (folic acid, pyridoxine, and biotin; ranges from 0 to about 10 ml/L). Alternatively, as semi-defined (complex) media may include, in addition to what was in the defined media, yeast extract and tryptone (animal-derived). Both yeast extract and tryptone range from 0 to about 0.4% w/v. Also included were sodium molybdate, magnesium sulfate, sodium chloride, EDTA, MOPS (3[N-morpholino] propane-sulfonic acid), amino acids (including L-methionine), and vitamins (folic acid, pyrodoxine, and biotin).

A type of fermentation according to the embodiment of the present disclosure is fed-batch fermentation, in which the cell growth rate is controlled by the addition of nutrients to the culture during cell growth. As used herein, "fed-batch fermentation" refers to a cell culture process in which the growth rate is controlled by carefully monitored additions of metabolites to the culture during fermentation. Fed-batch fermentation according to the present disclosure permits the cell culture to reach a higher biomass. The key to fed-batch fermentation is supplying substrate at a rate such that it is completely consumed. As a result, residual substrate concentration is approximately zero and maximum conversion of substrate is obtained. Metabolic overflow from excess substrate is avoided, reducing the formation of inhibitory acetate. Fed-batch fermentation starts with a batch phase. Cells are inoculated into an initial volume of medium that contains all non-limiting nutrients and an initial concentration of the limiting substrate. Controlled feeding of the limiting nutrient begins once the cells have consumed the initial amount of substrate. One of the simplest and most effective feeding strategies is exponential feeding. This method allows the culture to grow at a predetermined rate less than the population doubling time, as expressed herein, as mu $(\mu)_{max}$ without the need of feedback control. The fermentation begins with a batch mode containing a non-inhibitory concentration of substrate. The cells grow at mu $(\mu)_{max}$ until the substrate is exhausted, at which point the nutrient feeding begins.

The DO-stat and pH-stat methods are fairly easy to implement since most standard fermentor systems include dissolved oxygen and pH monitoring. Trends in dissolved oxygen (DO) and pH can indicate whether substrate is available to the cells. Exhaustion of substrate causes decreased oxygen uptake and the DO concentration in the medium rises. The pH also rises due to consumption of metabolic acids. Feeding is triggered when DO or pH rises above a set threshold. The growth rate can be adjusted by changing the DO or pH threshold value.

EXAMPLES

Reference will now be made in detail to certain embodiments of the present disclosure. While the present disclosure will be described in conjunction with the illustrated embodiments, it will be understood that they are not intended to limit the present disclosure to those embodiments. On the contrary, the present disclosure is intended to cover all alternatives, modifications, and equivalents that may be included within the present disclosure as defined by the appended claims. The headings below are not meant to limit the disclosure in any way; embodiments under any one heading may be used in conjunction with embodiments under any other heading. Nucleotide and amino acid sequences are referred to herein by a sequence identifier number (SEQ ID NOS:1 to 39). A sequence listing is provided at the end of the specification.

GDF5-T5 and GDF5-Trc Plasmid/Expression Vector Construction

Figure 1B:
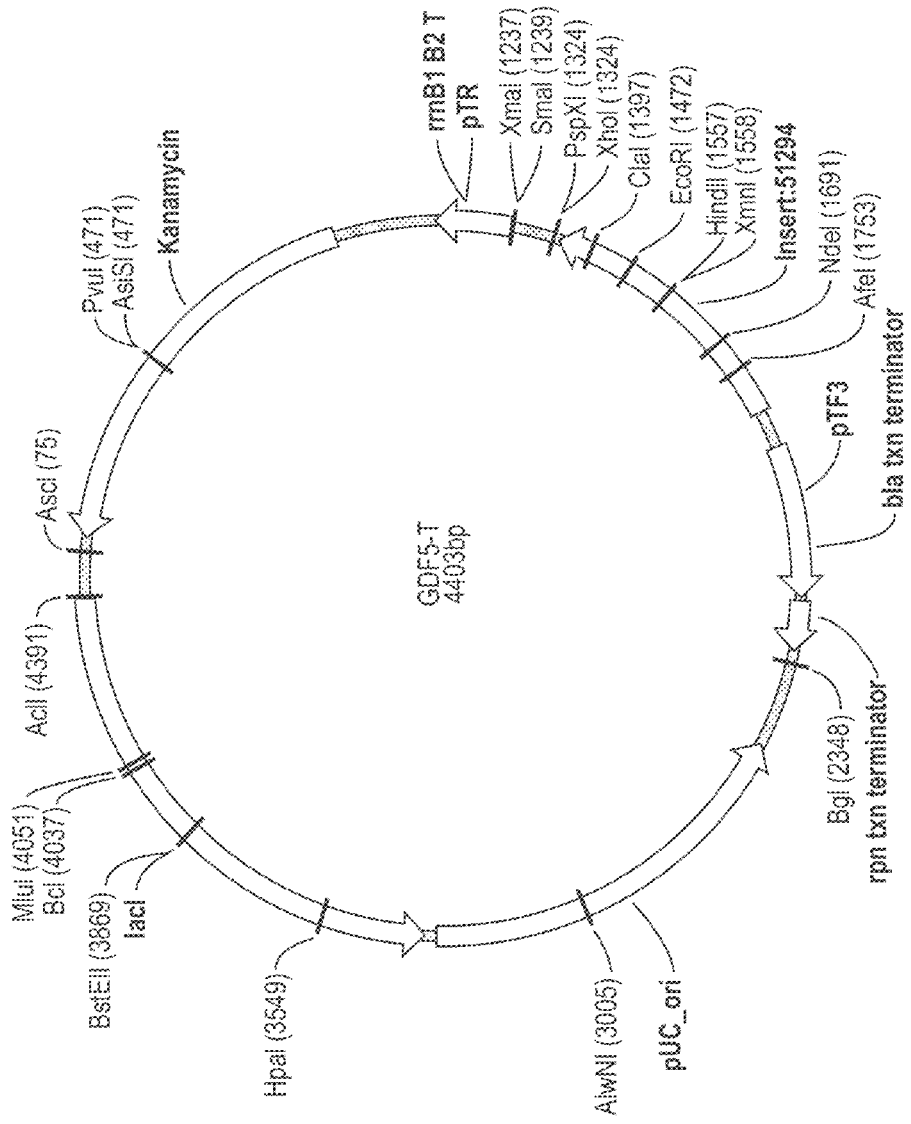

Two plasmid expression vectors (pGDF5-T5 and pGDF5-Trc) were engineered for the purpose of expressing a recombinant human growth and differentiation factor-5 (rhGDF-5) of about 13.5 kDa in selected prokaryotic host cell strains. Plasmid maps for both plasmids are provided in FIGS. 1A and 1B. The sizes of pGDF5-T5 and pGDF5-Trc are 4299 and 4403 bp, respectively. The complete nucleotide sequence of the pGDF5-T5 and pGDF5-Trc is designated in the Sequence Listing as SEQ ID NOS: 2 and 3, respectively.

To do this, a starting IP constraint-free plasmid, pJExpress-401 (DNA2.0, Menlo Park, Calif. having either a T5 or a Trc promoter (both IPTG-inducible) was employed. Some of the features of pJExpress-401 include a pUC origin, a Kanamycin selective marker gene ($Kan^R$) gene, either a T5 or a Trc promoter (both IPTG (isopropylthio-β-galactoside)-inducible) and an Nde-1 restriction site. The gene of interest (gene insert) is a codon-optimized human GDF-5 (rhGDF-5) cDNA having a size of 528 bp designated in the Sequence Listing as (SEQ ID NO:1). The reverse complimentary coding sequence of the insert sequence, as underlined is provided in the sequence listing as SEQ ID NO:7.

Plasmid DNA Analysis

As indicated above, the complete DNA sequences for pGDF5-T5 and pGDF5-Trc are provided in the sequence listing as SEQ ID NOS:2 and 3, respectively. The theoretical protein sequence encoded by pGDF5-Trc is denoted herein as SEQ ID. NO. 4. Sequencing was performed on pGDF5-T5 and pGDF5-Trc with a minimum of 2× coverage over the backbone and 4× coverage over the gene of interest (GDF-5

DNA insert). The samples were run on the ABI 3130×1 genetic analyzer and analyzed using ABI's Sequencing Analysis software version 5.3.1. The sequences were edited using Sequencher™ version 5.0. The sequences obtained were assembled into contiguous sequence files. The consensus sequence (MD1.seq corresponding to SEQ ID NO:3) was compared with the corresponding expected reference sequence file (MD1.txt corresponding to SEQ ID NO:6). The sequence file comparisons and additional data are discussed hereinbelow.

Plasmid DNA and Sequencing Primers Preparation and Purification:

Prior sequencing, the concentration of purified plasmid GDF5-Trc and GDF5-T5 DNA (pGDF5-Trc and pGDF5-T5) was determined using the Smartspec™ 3000 spectrophotometer. Sequencing Primers (oligonucleotides) were designed accordingly and the following primers, as well as the polynucleotides and polypeptides according to the embodiments of the present disclosure, are listed on Table 1. The sequencing primers were utilized to sequence pGDF5-Trc.

TABLE 1

| SEQ ID NO. | Description | Sequence | Species/Type | Length | Start | Direction | Tm | % GC |
|---|---|---|---|---|---|---|---|---|
| 1 | GDF-5 DNA insert-insert DNA from pGDF5-Trc plasmid | See Sequence Listing | human/DNA | 528 | | | | |
| 2 | complete sequence of pGDF5-T5 DNA | See Sequence Listing | human/DNA | 4299 | | | | |
| 3 | complete sequence of pGDF5-Trc DNA | See Sequence Listing | human/DNA | 4403 | | | | |
| 4 | theoretical amino acid sequence of rhGDF-5 protein | See Sequence Listing | human/protein | 125 | | | | |
| 5 | GDF5-CofA from Prospec-TanyTechnoGene Ltd | See Sequence Listing | human/protein | 120 | | | | |
| 6 | MD1.txt reference GDF-5 sequence for Sequencing | See Sequence Listing | human/DNA | 4405 | | | | |
| 7 | Reverse complementary strand insert sequence from pGDF5-Trc plasmid | See Sequence Listing | human/DNA | 528 | | | | |
| 8 | MDP1.1SF1-A | CTATCATGCCATACCGCGAAA | artificial sequence | 21 | 35 | Forward | 60 | 48 |
| 9 | MDP1.2SF1-A | GCCAGCCATTACGCTCGTC | artificial sequence | 19 | 382 | Forward | 60 | 63 |
| 10 | MDP1.3SF1-A | CGCTACCTTTGCCATGTTTCA | artificial sequence | 21 | 721 | Forward | 60 | 48 |
| 11 | MDP1.4SF1-A | TAATCGCGGCCTCGACG | artificial sequence | 17 | 857 | Forward | 60 | 65 |
| 12 | MDP1.5SF1-A | CCTGACCCCATGCCGAA | artificial sequence | 17 | 1105 | Forward | 60 | 65 |
| 13 | MDP1.6SF1-A | AGTTAGCGACAGCCGCAGC | artificial sequence | 19 | 1328 | Forward | 60 | 63 |
| 14 | MDP1.7SF1-A | ATGGCTACGCAGCGGAAAC | artificial sequence | 19 | 1516 | Forward | 60 | 58 |
| 15 | MDP1.8SF1-A | GCGGCATATGTTTTACCTCCTG | artificial sequence | 22 | 1686 | Forward | 59 | 50 |
| 16 | MDP1.9SF1-A | AGCTCGTAATTGTTATCCGCTCA | artificial sequence | 23 | 1812 | Forward | 59 | 43 |
| 17 | MDP1.10SF1-A | CAAGCAAAGTGACAGGCGC | artificial sequence | 19 | 2214 | Forward | 59 | 58 |
| 18 | MDP1.11SF1-A | GGCGGTAATACGGTTATCCACA | artificial sequence | 22 | 2542 | Forward | 60 | 50 |
| 19 | MDP1.12SF1-A | TGCGCCTTATCCGGTAACTATC | artificial sequence | 22 | 2933 | Forward | 59 | 50 |
| 20 | MDP1.13SF1-A | TTTTGGTCATGAGTCACTGC | artificial sequence | 20 | 3311 | Forward | 53 | 45 |

TABLE 1 -continued

| SEQ ID NO. | Description | Sequence | Species/Type | Length | Start | Direction | Tm | % GC |
|---|---|---|---|---|---|---|---|---|
| 21 | MDP1.14SF1-A | GGAACGATGCCCTCATTCAG | artificial sequence | 20 | 3691 | Forward | 59 | 55 |
| 22 | MDP1.15SF1-A | CCAGCGGATAGTTAATGATCAGC | artificial sequence | 23 | 4022 | Forward | 59 | 48 |
| 23 | MDP1.16SF1-A | CCGGCATACTCTGCGACATC | artificial sequence | 20 | 4366 | Forward | 60 | 60 |
| 24 | MDP1.17SR1-A | GATGTCGCAGAGTATGCCGG | artificial sequence | 20 | 21 | Reverse | 60 | 60 |
| 25 | MDP1.18SR1-A | CATTAACTATCCGCTGGATGACC | artificial sequence | 23 | 368 | Reverse | 59 | 48 |
| 26 | MDP1.19SR1-A | GCCAACGATCAGATGGCG | artificial sequence | 18 | 732 | Reverse | 60 | 61 |
| 27 | MDP1.20SR1-A | TGACCAAAATCCCTTAACGTGAGT | artificial sequence | 24 | 1087 | Reverse | 60 | 42 |
| 28 | MDP1.21SR1-A | GATAGTTACCGGATAAGGCGCA | artificial sequence | 22 | 1452 | Reverse | 59 | 50 |
| 29 | MDP1.22SR1-A | CCTGCGTTATCCCCTGATTCT | artificial sequence | 21 | 1823 | Reverse | 59 | 52 |
| 30 | MDP1.23SR1-A | AAACGACGGCCAGTCTTAAGCT | artificial sequence | 22 | 2029 | Reverse | 60 | 50 |
| 31 | MDP1.24SR1-A | AACGTAAAAACCCGCTTCGG | artificial sequence | 20 | 2099 | Reverse | 60 | 50 |
| 32 | MDP1.25SR1-A | CGCCTGTCACTTTGCTTGATA | artificial sequence | 21 | 2175 | Reverse | 58 | 48 |
| 33 | MDP1.26SR1-A | TGAGCGGATAACAATTACGAGCT | artificial sequence | 23 | 2572 | Reverse | 59 | 43 |
| 34 | MDP1.27SR1-A | TTGCTCCCGTAAAGCCCTG | artificial sequence | 19 | 2767 | Reverse | 60 | 58 |
| 35 | MDP1.28SR1-A | CCCGATCTCTATTCTGTTCATCG | artificial sequence | 23 | 2986 | Reverse | 59 | 48 |
| 36 | MDP1.29SR1-A | TACGGCGTTTCACTTCTGAGTTC | artificial sequence | 23 | 3265 | Reverse | 59 | 48 |
| 37 | MDP1.30SR1-A | GGTGCGACAATCTATCGCTTG | artificial sequence | 21 | 3613 | Reverse | 59 | 52 |
| 38 | MDP1.31SR1-A | GATCGCGTATTTCGCCTCG | artificial sequence | 19 | 3934 | Reverse | 60 | 58 |
| 39 | MDP1.32SR1-A | CTGCCTCGGTGAGTTTTCTCC | artificial sequence | 21 | 4206 | Reverse | 60 | 57 |

The sequencing primers were diluted to a final concentration of 1.6 pmol/pL and the cycle sequencing reactions were setup in a 96-well plates. The cycle sequencing plates were then loaded onto the ABI Veriti® Thermal Cycler for a cycle sequencing run based on the following cycling conditions (see Table 2):

TABLE 2

| Cycling Conditions: | |
|---|---|
| 98° C. | 5 minutes |
| 30 cycles: | 96° C., 30 seconds |
| | 50° C., 10 seconds |
| | 62° C., 4 minutes |
| Hold: | 4° C., 00 |

Sample purification (dye terminator removal) occurred after the cycle sequencing run. The samples were purified using Qiagen® Dye Ex 2.0 Spin Kit. The samples were eluted with Hi-Di Formamide and transferred to 96-well plates. The 96-well plates were denatured at 95° C. for 2 minutes in the ABI Veriti® Thermal Cycler.

Sequencing Analysis:

The 96-well sequencing plates were run on the ABI 3130×1 Genetic Analyzer using ABI's Data Collection Software version 3.0. The sequencing data (electropherograms) were analyzed using ABI Sequence Analysis software version 5.3.1. The sequences were edited and assembled into contiguous sequence files using Sequencher™ Version 5.0. The following ambiguity codes may appear in the sequence files:

TABLE 3

| Symbol: | Meaning: |
|---|---|
| 1 | Probable C |
| 2 | Probable T |
| 3 | Probable A |
| 4 | Probable G |
| R | A or G |
| Y | C or T |
| M | A or C |
| K | G or T |
| W | A or T |
| S | G or C |
| H | A or C or T |
| B | G or T or C |
| V | G or C or A |
| D | G or T or A |
| N | A, C, G, or T |

DNA Sequencing Analysis Summary:

Of the 4405 bps provided, 4403 bps was sequenced. The plasmid pGDF5-Trc DNA, designated herein as SEQ ID NO:3 was sequenced in full with a minimum of 2× coverage over entire plasmid and 4× coverage over the insert (bp 1324-4851). The insert sequence was conforming and there were 3 discrepancies found outside the coding region (DNA insert): (i) one (1) ambiguity (Y at consensus position bp: 116) and 2 discrepancies (ii) two (2) deletions in supplied sequence (bases that appear in sequence (MD1.txt of SEQ ID NO:6)) but not in the sequenced data (MD1.seq of SEQ ID NO:3)) at consensus positions bp: 86 and 87). Protein alignment between the theoretical amino sequence encoded by pGDF5-

Trc shows that it is about 99% identical to the amino acid sequence of a commercially-known recombinant human GDF-5 protein (Catalog No. CYT-442; Prospec-TanyTechnoGenei Ltd, Rehovot, Israel). See FIG. 1C and Sequence ID NOS:4 and 5, respectively).

pGDF5-T5 and pGDF5-Trc Transformation

Four *Escherichia coli* bacteria host cell lines were selected for pGDF5-T5 and pGDF5-Trc transformation: (1) DH10β (genotype: F-, mcrA Δ(mrr-hsdRMS-mcrBC) φ80lacZΔM15 ΔlacX74 recA1 endA1 araD139 Δ (ara, leu)7697 galU galK λ-rpsL nupG/pMON14272/MON7124); (2) STBL2 (genotype: F-, mcrA Δ(mcrBC-hsdRMS-mrr) recA1 endA1lon gyrA96 thi supE44 relA1 λ-Δ(lac-proAB); (3) HMS174 (genotype: F-, recA1 hsdR(rK12-mK12+)(RifR); and (4) recA (genotype: recA1819 complete gene deletion).

A. Preparation of Media and Agar Plates

"Select APS (Alternative Protein Source) LB Media" was prepared by dissolving 20 g of Select APS LB broth base powder in 1 L of purified water with a pH that ranged from about 6.6 to about 7.1. LB agar plates were prepared by adding 7.5 g of Agar, U.S.P. into 500 mL of Select APS LB media. Both APS LB media and agar were autoclaved for 121° C. to 123° C. for ≥45 min on liquid cycle. After cooling to 40-60° C., Kanamycin antibiotic was added to the media and agar plates at a concentration of 50 μg/mL.

B. Host Cell Transformation

Plasmid GDF5-T5 or pGDF5-Trc DNA (SEQ ID NOS:2 and 3, respectively) and a competent cell *E. coli* host cell, either from strain DH10β, STBL2, HMS174 or recA, were each separately mixed together in a tube and incubated on an ice bath for at least about 30 minutes, heat shocked for 45 seconds at 42° C.±2° C.) and immediately placed on ice for 2-5 min. About 450 μl of SOC media (Bacto tryptone 20 g/L; Bacto yeast extract, 5 g/L; NaCl, 0.5 g/L; $MgCl_2.6H_2O$ 2.03 g/L; glucose 3.6 g/L) was then added into each bacteriaplasmid DNA mixture and placed onto 37° C. (±1° C.) shaker incubator and shaked at about 225 to about 275 rpm for 60 minutes (±5 minutes). To prevent lowering of a dissolved oxygen concentration, the shaker incubator was sped up to keep the dissolved oxygen concentration at 50% of air saturation. After 1 hour, an aliquot of the transformed cells were aseptically plated into APS LB/Kn agar plates and incubated overnight at 37° C. (±1° C.) for about 14 to about 24 hours. The cultivation was proceeded by adding 50% glucose solution at a level of 0.2% to obtain a high cell density, with an indication of abrupt increase of the dissolved oxygen concentration. The final pH of the growth medium was at about a pH of 7.

Table 4 lists the different transformed groups with their corresponding host cell strain and vector constructs:

TABLE 4

| Transformed Groups | Host Cell Line | Vector Construct |
| --- | --- | --- |
| A | DH10β (Clones 1-5) | pGDF5-T5 |
| B | DH10β (Clones 1-5) | pGDF5-Trc |
| C | STBL2 (Clones 1-5) | pGDF5-T5 |
| D | STBL2 (Clones 1-5) | pGDF5-Trc |
| E | HMS174 (Clones 1-5) | pGDF5-T5 |
| F | HMS174 (Clones 1-5) | pGDF5-Trc |
| G | recA (Clones 1-5) | pGDF5-T5 |
| H | recA (Clones 1-5) | pGDF5-Trc | pGDF5-T5 and pGDF5-Trc constructs were each successfully transformed into each four host cell lines. Clonal selection and expression screening were conducted by first performing a small scale fermentation with IPTG induction (1 mM final concentration). For STBL2, clonal selection was performed at 30° C. The presence of pGDF5-T5 or pGDF5-Trc DNA (SEQ ID NOS:2 and 3, respectively) was each confirmed by restriction enzyme analysis with NdeI. GDF5 protein analysis was assessed through SDS-PAGE and Western blotting To monitor the transformation process, a positive (+) control vector construct, pJExpress, was used. A clone that expresses the pJExpress construct showed an over-expression of a fluorescent protein of about 30 kDa protein after IPTG induction (data not shown).

Expression Screening of pGDF5-T5 and pGDF5-Trc Constructs

Figure 2A:
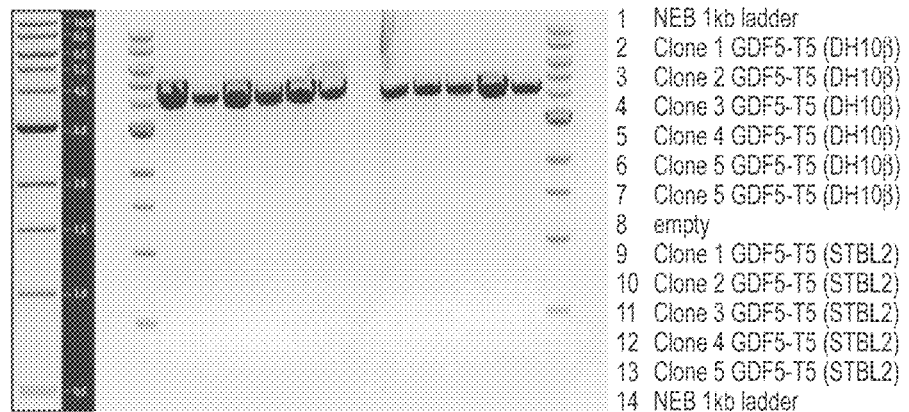
FIGS. 2A and 2B are agarose gels showing NdeI-linearized plasmid DNAs prepared from pGDF5-T5- and pGDF5-Trc-transformed DH10β and STBL2 clones.
Figure 2B:
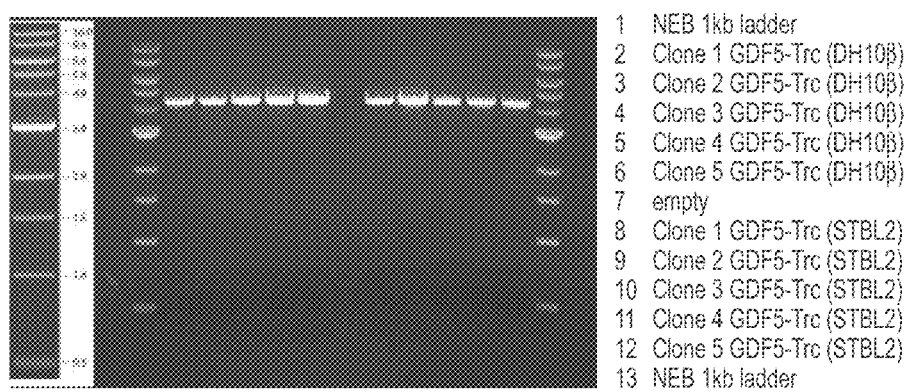

A. DNA-Restriction Enzyme Analysis:

Five bacterial colonies (Clones 1-5) from each transformed groups, Groups A-H as listed in Table 4, were initially picked for overnight growth in APS LB media containing 50 μg/ml of Kanamycin (APS LB/Kan). The next day, two (2 ml) of APS LB/Kan bacterial culture from each colony of each transformed groups, were grown at 37° C. (±1° C.) overnight. Plasmid DNAs were extracted and purified using a QIAprep® Spin Miniprep Kit (Qiagen, Inc, Valencia, Calif.). The purified DNAs were linearized with NdeI restriction enzyme and run through a 0.8% agarose gel to verify for the presence of the pGDF5-T5 and pGDF5-Trc constructs. Both linearized pGDF5-T5 and pGDF5-Trc DNAs have an expected size of 4299 bp and 4403 bp, respectively. As shown in FIGS. 2A and 2B, successful transformation of pGDF5-T5 and pGDF5-Trc DNA into DH10β and STBL2 (grown at 30° C.) host cells clones 1-5, respectively, was confirmed. Transformation of pGDF5-T5 and pGDF5-Trc (Clones 1-5, respectively) on HMS174 and recA host cell strains was also successful, the results of which are not presented herein.

B. Preparation of *E. coli* Inclusion Bodies (IB)

Positive transformants from each Group (A-H) as listed in Table 4 were cultured according to the above-mentioned method. Cells from the culture broth of each transformant were harvested and resuspended in TE buffer (25 mM Tris and 10 mM EDTA, pH 7.3). To collect inclusion bodies that contain the highly purified concentrated rhGDF-5 protein, cells were broken up by means of a homogenizer and spun down to collect the pellet (or precipitate) that contains the inclusion bodies. The inclusion bodies were washed with wash buffer and centrifuged for a period of time at 4° C. The collected pellet was solubilized by sonicating in solubilization buffer. After solubilization, the solution containing the rhGDF-5 protein was centrifuged for a period of time at 4° C.

To obtain high purity with the highest maximum yield rhGDF-5 protein yet low oxidation and minimal related impurities, the resultant supernatant was subjected to a weak cation exchanger resin, Toyopearl™ CM-650 from Tosoh Bioscience LLC, King of Prussia, Pa. Briefly, the CM-650 column was first equilibrated with buffer before the resultant supernatant was applied to the CM-650 column. The CM-650 column was washed before eluting with the same buffer modified with a salt to elute the proteins off the column. In various embodiments, Toyopearl™ CM-650 may be replaced by Amberlite® IRC86, CM agarose-based material and/or Dowex® as the weak cation exchanger resin.

In various embodiments, various washing buffers can be used during the purification process such as, for example, phosphate buffer saline (PBS). In some embodiments, GDF-5 protein purity is approximately 95%, 96%, 97%, 98%, 99% and/or 100%.

C: SDS-PAGE and Western Blotting

To screen for bacterial clones capable of expressing rhGDF-5 protein, five single colonies from each group as listed in Table 1, were further inoculated in 4 ml of APS LB agar plates containing 50 μg/ml of Kanamycin (APS LB/Kan) and grown at 37° C. When the bacterial culture grew to $OD_{600}$ from about 0.4 to about 0.6, they were induced with or without IPTG (1 mM final concentration; ±IPTG). Non-induced and Induced cultures were each harvested and treated with Novagen™ BugBuster Protein Extraction Reagent. Supernatant (soluble proteins) and pellet (insoluble proteins) from each culture, either IPTG-induced or uninduced, were then analyzed by SDS-PAGE.

For SDS PAGE, a total of 20 μL sample (13 μl of sample, 2 μl of reducing agent and 5 μl of sample loading buffer) was prepared for gel loading. The 20 μL-samples were boiled at 95° C. for 5 minutes and loaded either as 5 μl or 20 μl for larger volume loading. All positive clones showed the presence of the expected 13.5 kDa rhGDF-5 protein.

rhGDF-5 expression was observed in the pellets of clones from all of the host cell strains tested, regardless of which vector constructs was used in the transformation. Overexpression of rhGDF-5 protein was particularly observed in clones from HMS174 and RecA strains and was better than those of DH10β and STBL2 ((data not shown). In addition, a higher rhGDF-5 over-expression was observed with longer IPTG induction time (results not included). The size-wise comparison of the over-expression band with the reference protein, rhGDF5 was further confirmed by Western blotting analysis using an anti-human GDF-5 antibody.

From the Western blot results obtained, GDF-5 protein was found in the bacterial pellet fraction (see FIG. 3B) and not in the supernatant fraction (see FIG. 3A). Also, the expression level using the GDF5-TRC construct was better than that of pGDF5-T5 construct. Among the 4 different host cell lines expressing pGDF5-TRC, the HMS174 cell strain provided the optimally-expression levels of the GDF-5 protein.

Characterization of the Over-Expressing GDF-5 Clones

About 400 μl±2% of thawed pGDF5-Trc- or pGDF5-T5-transformed clones were aseptically and inoculated into two separate flasks of pGDF5-T5 and pGDF5-Trc-transformed RecA or HMS174 (Flask 1 for growth monitoring and Flask 2 for storage processing) in the growth medium. Each of the inoculated flasks were shaked at 220 to 250 rpm at a temperature of about 37° C.±1° C. until an optical density ($OD_{600}$) of about 1 to about 3 was reached. After 8 hours of fermentation (EFT8; Elapsed Fermentation Time), hourly sampling from Flask 1 was taken for optical density measurements. Sampling may occur prior to EFT 8 and when $OD_{600}$ of Flask 1 reached between 0.8 and 1.0, the $OD_{600}$ of Flask 2 was also measured.

Figure 4A:
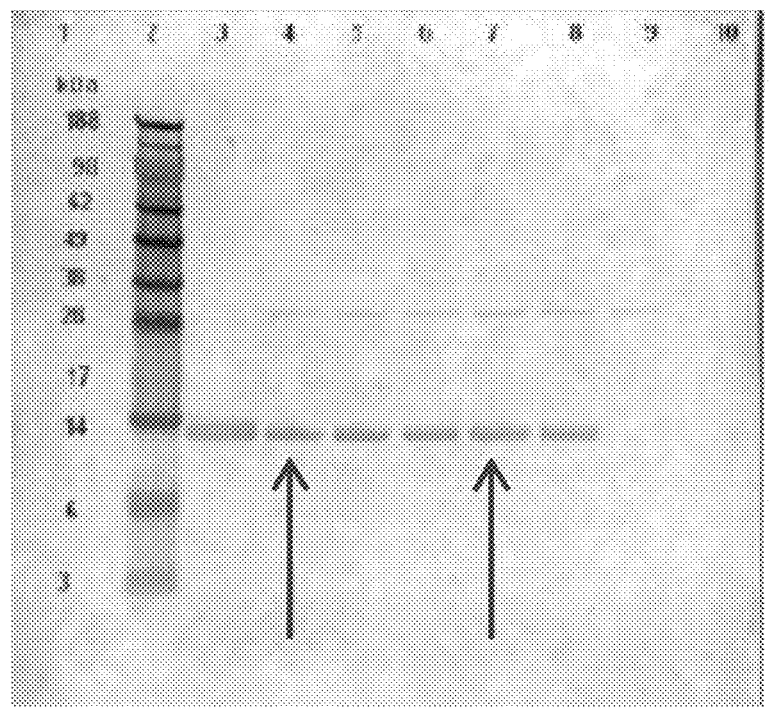
FIG. 4A is a Western blot showing over-expression of GDF-5 in pGDF5-Trc-transformed Clones 1 and 4.
Figure 4B:
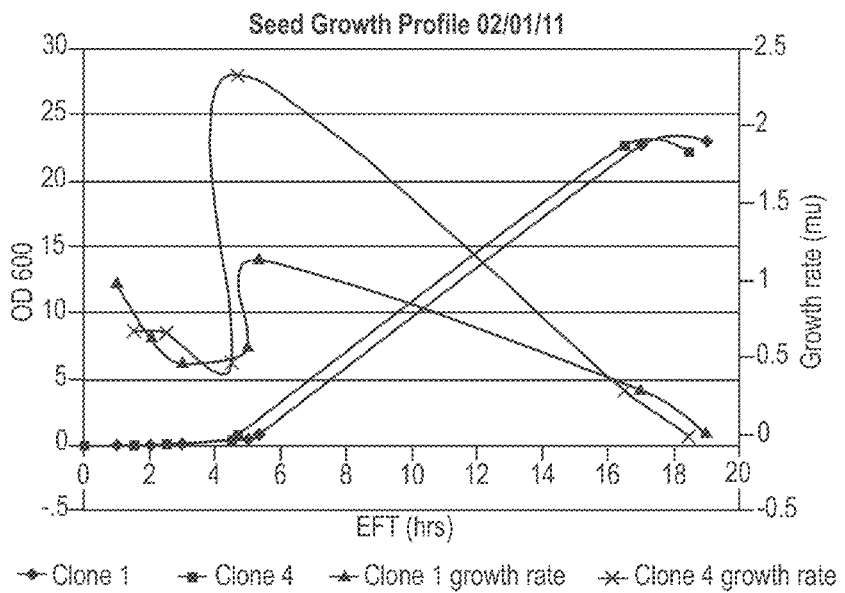
FIG. 4B shows the growth profile and rate of pGDF5-Trc-transformed HMS174 Clones 1 and 4.

Of the forty clones (5 clones per each transformed group) examined, two clones, Clones #1 and 4 derived from pGDF5-TRC-transformed HMS174, were selected and evaluated for further studies, e.g., ability to express and produce GDF-5 and growth profile and rate (see FIGS. 4A and 4B, respectively).

The growth profile study was done to understand how these cells grow in the lag, exponential and stationary phases. The data obtained may then allow for profiling growth rates, population doubling time (expressed as μ), carbon consumption and waste production.

Growth rate constant, according to the embodiment of the present disclosure, can be defined as the number of generations that occur per unit time (expressed as μ or mu), where (1) $\mu = (\ln N2 - \ln N1)/(t2-t1)$ where N2 and N1=cells ml−1 at time t2 and t1 (in h); and (2) convert (1) to log: $\mu = (\log N2 - \log N1)(2.303)/t2$ and t1).

As depicted in FIG. 4A, pGDF5-Trc-transformed HMS174 Clones 1 and 4 both overexpress the rhGDF-5 protein. However, the growth profile of Clone 4 was better than that of Clone 1 (with Clone 4 having a higher mu or μ value for growth rate), despite the similarity in their $OD_{600}$ values starting from EFT0 to EFT18.5-19.0 (see FIG. 4B). Growth characterization and protein production were further conducted by growing the transformants using two fermentation methods: (1) ultra yield shake flask (UY SF) and (2) 5 L Applikon Fermentor (Ferm).

The ultra yield shake flask (UY SF) fermentation method, as discussed above, may be used to easily make the recombinant protein material without the use of a fermentor. This technology is disposable, and is product dedicated. It stimulates a fermentation environment but does not require the infrastructure and laborious setup that actual bioreactor fermentations need. It has a similar set up like a disposable shake flask and allows for the manufacturing of the recombinant protein material that is closely representative of what can be made in a fermentor to support downstream and analytical development of the recombinant protein The 5 L fermentation method, on the other hand, is a non-GMP batch induction fermentation method for production of the recombinant GDF-5 protein. It involves the inoculation of 400 mL of seed media with 1000 μl seed ampoule of pGDF5-Trc-transformed Clone 1 or 4 and shaking the media at 250 rpm, for 8 hrs at 37° C. This was followed by inoculating about 200 mL of seed culture into the 5-L fermenter with the following fermentation parameters:

Fermentation Parameters: Temperature 37° C., Stirring: 330-1322 rpm, Airflow: 4 L/min, pH control: 6.8+/−0.2 with ammonium hydroxide and 50% phosphoric acid, dissolved oxygen: 30%, and anti-foam 204 as needed.

When the $OD_{600}$ reaches at about 0.6-0.8, 1 mM IPTG was added for induction. After 14-18 hours of post-induction, the bacterial culture was harvested.

Figure 5A:
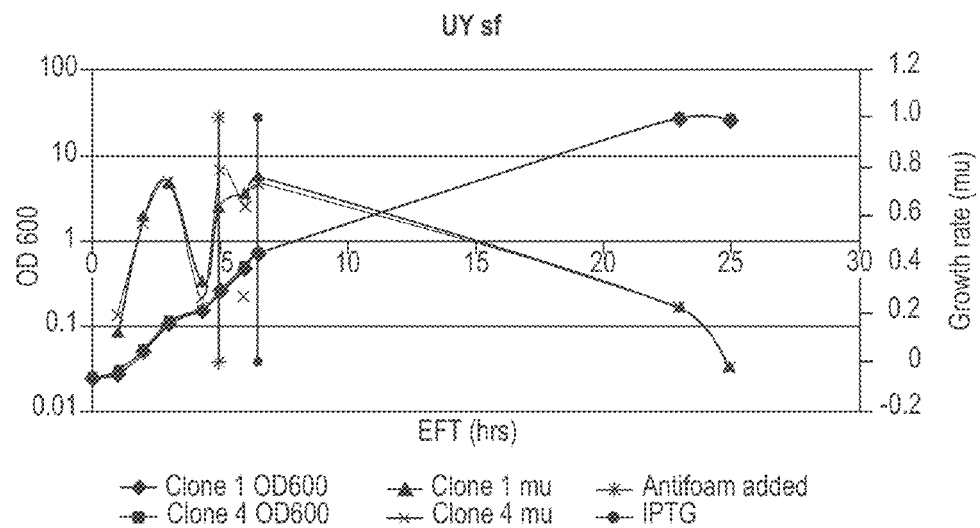
FIGS. 5A and 5B shows the growth profiles of pGDF5-Trc-transformed HMS174 Clones 1 and 4 when grown using the ultra yield shake flask and 5 L Applikon Fermentor, respectively.
Figure 5B:
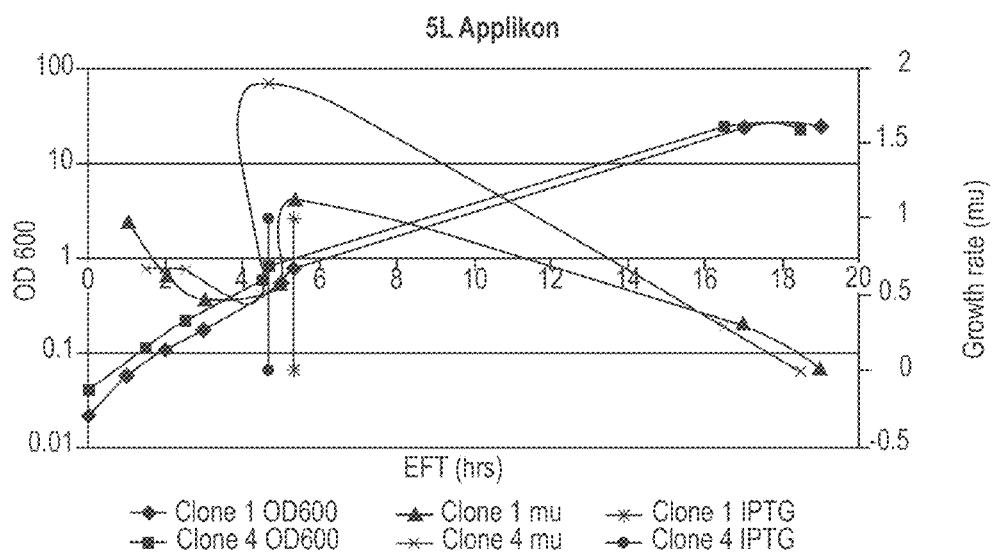

The goal for exploring these methods is to develop a recombinant protein production that is not laborious and simple for analytical and purification approach. These two methods vary in terms of the following as illustrated in Table 5 and in the results obtained as shown in FIG. 5A and FIG. 5B.

TABLE 5

|  | UY Shake Flask (FIG. 6A) | 5L Applicon Fermentor (FIG. 6A) |
|---|---|---|
| pH Control | APS Super Broth with 100 mM MOPs | APS Super Broth with H3PO4 and NH4OH |
| pH Shift | pH shift to more acidic may cause protein induction | pH maintained at 7.0 ± 0.2 |
| Growth Rate | lower growth rate at induction | growth rate was above 1 at induction |

Figure 6A:
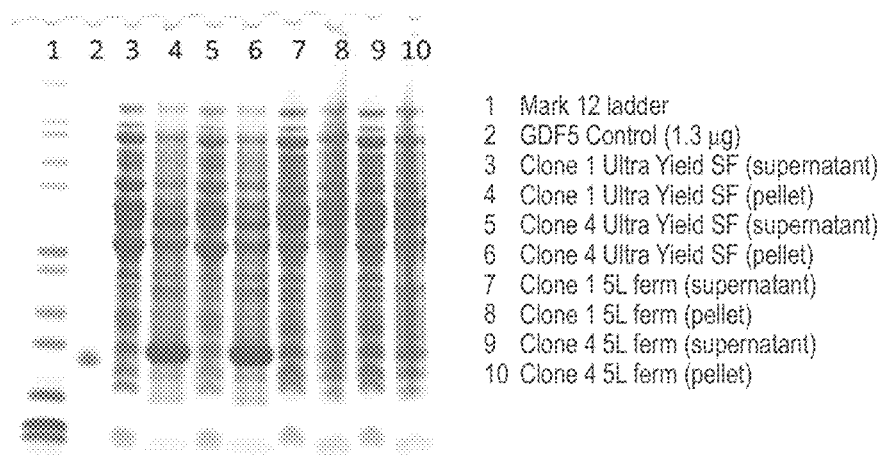
FIG. 6A is a Coomassie brilliant blue-stained gel showing GDF-5 protein production from supernatant and pellet fractions of pGDF5-Trc-transformed HMS174 Clones 1 and 4 that were grown by either using the ultra yield shake flask method or the 5 L Applikon Fermentor method.
Figure 6B:
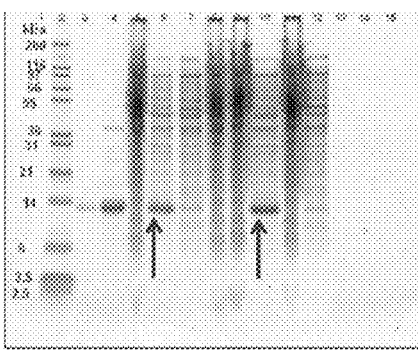
FIG. 6B is a Western blot showing GDF-5 over-expression from supernatant and pellet fractions of pGDF5-T5- and -Trc-transformed HMS174 Clones 1 and 4 that were grown by either using the ultra yield shake flask method or the 5 L Applikon Fermentor method.

A better GDF5 protein expression was observed when UY SF method was employed (see SDS-PAGE as shown in FIG. 6A), but the overall GDF5 expression may appear equivalent between Clones 1 and 4 (see western blot as shown in FIG. 6B, lanes 6 and 10). In addition, the pellet fraction from Clone 1 UY SF (sample PF030311A, lane 10) appeared to have a more dense GDF5-band (see FIG. 6B). Supernatant (soluble proteins) and pellet (insoluble proteins) samples from pGDF5-Trc-transformed Clones 1 and 4 were analyzed using SDS-PAGE and have the following designations:

TABLE 6

| Sample Source | Sample Description | Designated pGDF5-Trc Clone # |
|---|---|---|
| Supernatant | SF020311A | Clone 1 UY SF |
| Pellet | PF020311A | Clone 1 UY SF |
| Supernatant | SF020311B | Clone 4 UY SF |
| Pellet | PF020311B | Clone 4 UY SF |
| Supernatant | SF020311C | Clone 1 5L Ferm |
| Pellet | PF020311C | Clone 1 5L Ferm |
| Supernatant | SF020311D | Clone 4 5L Ferm |
| Pellet | PF020311D | Clone 4 5L Ferm |

Maximizing pGDF5-Trc DNA Yield and Optimal Recombinant GDF-5 Protein Production

High plasmid DNA yield and recombinant protein production, while still cost-effective, are important for the manufacturing of rhGDF-5 biologics. Therefore, to attain the maximum pGDF5-Trc DNA yield and rhGDF-5 protein production, efforts were made to obtain a high cell density fermentation for DNA production. Specifically, the type of production (batch, fed-batch or continuous fermentation), type of media and components and growth control strategies were considered. To achieve these goals, the inventors added several components or ingredients to a high cell density media (formulation as described in FIG. 7) to determine their effects of cell growth, GDF5-Trc DNA plasmid yield and rhGDF-5 protein expression without compromising GDF5-Trc plasmid quality and GDF-5 protein expression. A two level fractional factorial designed of experiment (DoE) was performed in Thomson 24-microwell plates using either a defined (minimal) or semi-defined (complex) media. Statistical software was employed to evaluate these various formulations for fermentation media.

A. Defined Media DoE (7-Factor DoE Design Space)

Figure 8A:
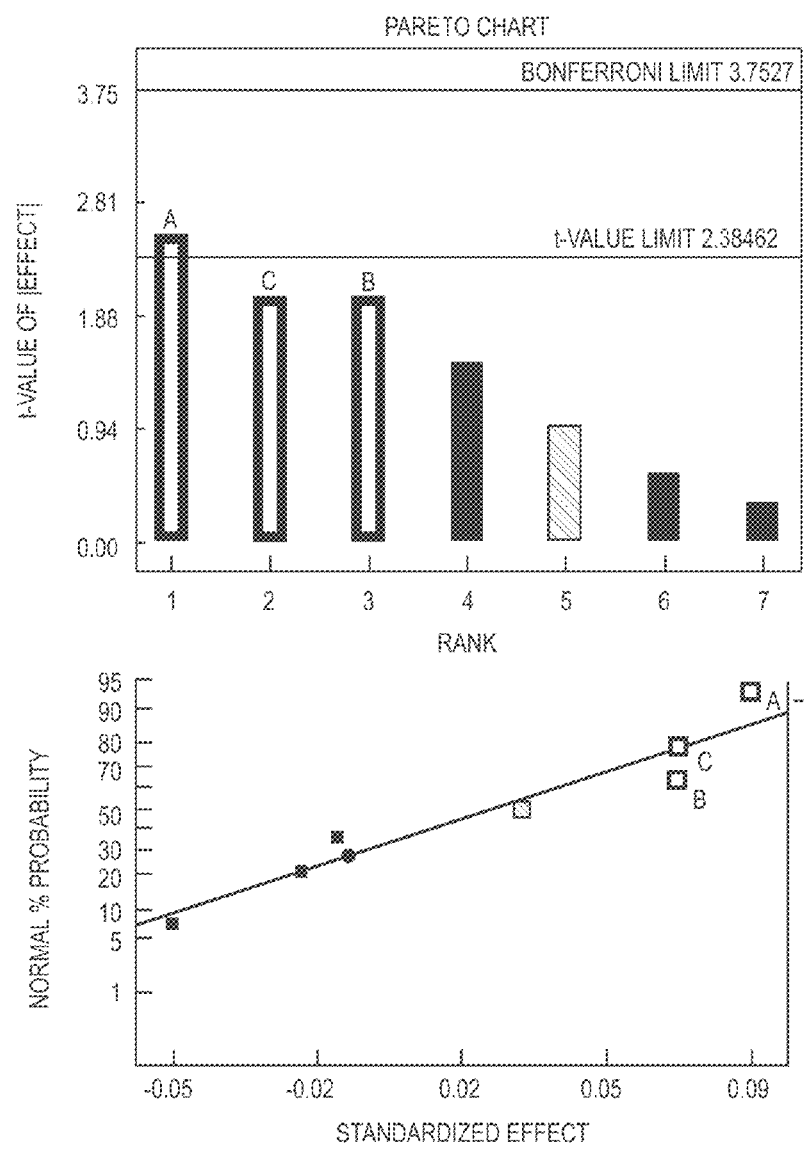
Figure 9A:
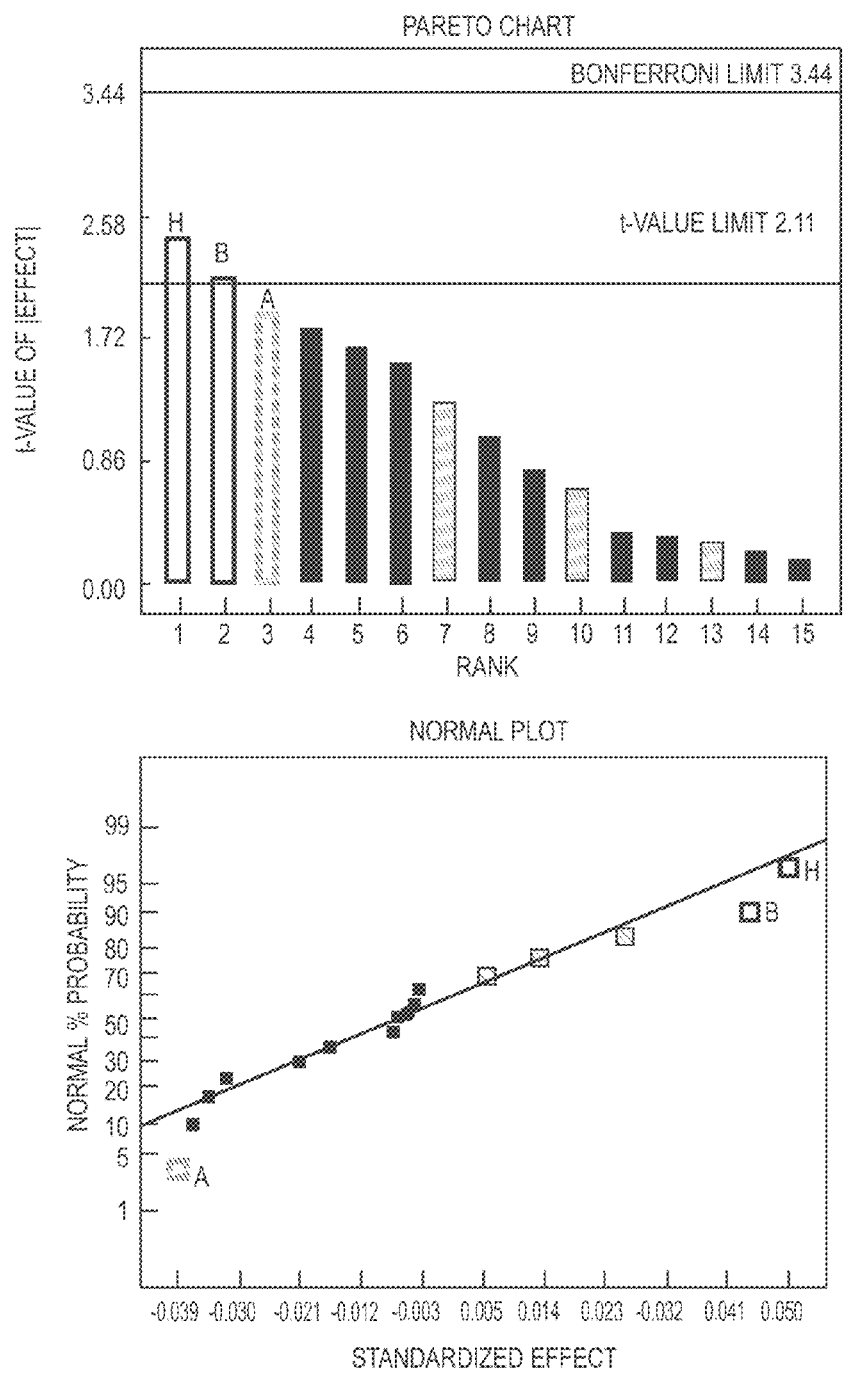
Figure 9D:
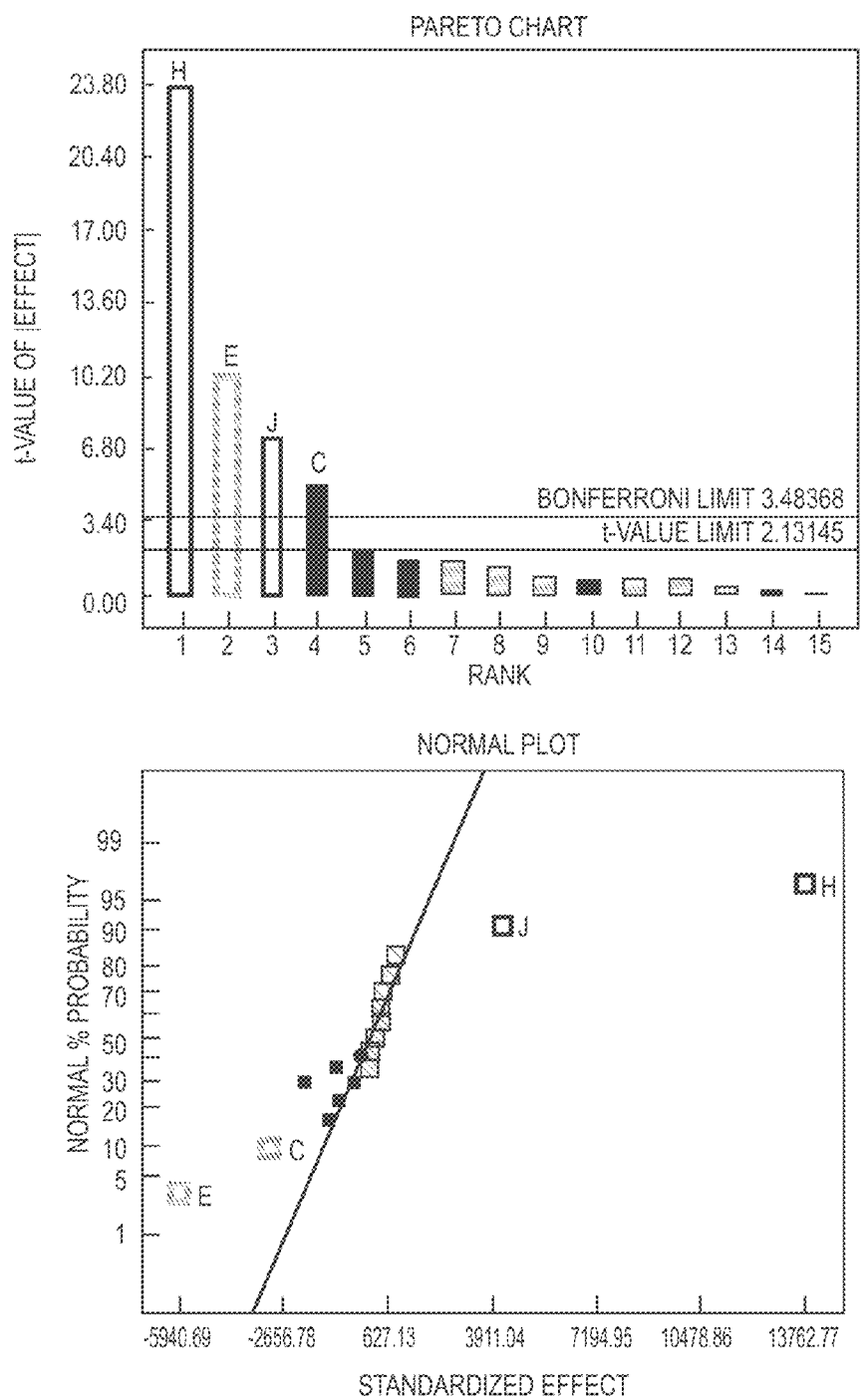
Figure 10:
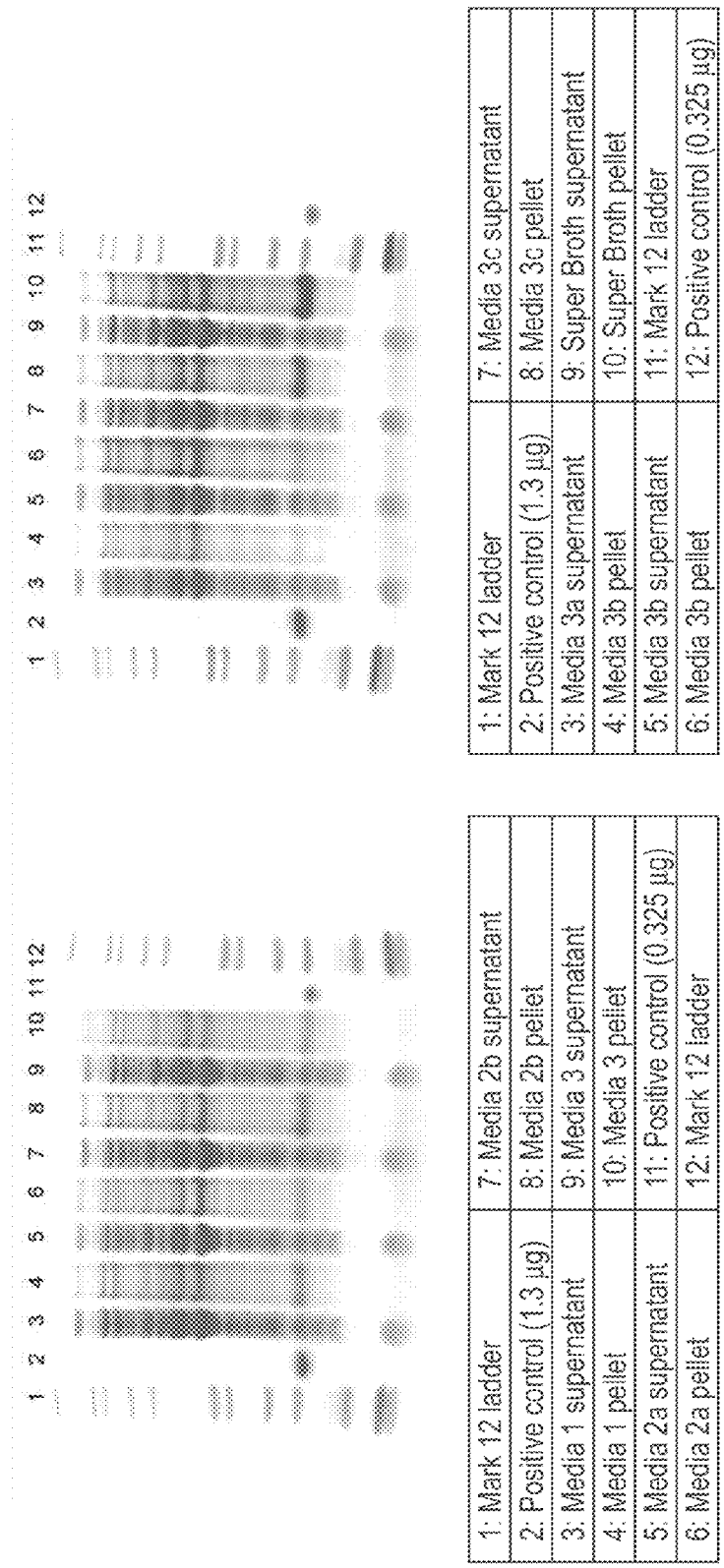
FIG. 10 is a Coomassie brilliant blue-stained gel showing the level of GDF-5 protein production of pGDF5Trc-transformed HMS174 cells when grown under different types high cell density media that were designed with respect to their optimized response to either rhGDF-5 expression (protein production) and biomass yield (growth rate): Media 1 (defined media improved rhGDF-5 expression); Media 2 (semi-defined media improved rhGDF-5 expression); and Media 3 (semi-defined media improved biomass yield).

The defined media additionally includes ingredients such as sodium molybdate (ranges from about 5 to about 10 mg/L), magnesium sulfate heptahydrate (ranges from about 2 to about 6 mM), sodium chloride (ranges from 0 to about 4 g/L), EDTA (ranges from 0 to about 400 mg/L), MOPS (ranges from 0 to about 100 mM), amino acid supplement including L-methionine (ranges from 0 to about 10 ml/L) and vitamin supplement (folic acid, pyrodoxine, and biotin; ranges from 0 to about 10 ml/L). Center points were added to detect for curvature and residual testing and lack-of-fit testing were included in the studies. The transformed bacteria were grown in Thomson 24-well microplate at 37° C., 250 rpm, induced after 4 hours of elapsed fermentation time (EFT4) with 1 mM IPTG and harvested after incubating for an additional 14 hours. Chemical lysis was performed on harvested samples. Bacterial pellet samples were run on SDS-PAGE. Gels were analyzed using ImageJ densitometry software (see FIGS. 8A-B).

B. Semi-Defined Media DoE

The semi-defined (complex) media included, in addition to what was in the defined media, yeast extract and tryptone (animal-derived). Both yeast extract and tryptone range from 0 to about 0.4% w/v. Also included were sodium molybdate, magnesium sulfate, sodium chloride, EDTA, MOPS (3[N-morpholino] propane-sulfonic acid), amino acids (including L-methionine), and vitamins (folic acid, pyrodoxine, and biotin). The center points were added to detect for curvature and residual testing were included. The transformed bacteria were grown in Thomson 24-well microtitreplate in high-throughput minibioreactor system at 37° C., 1000 rpm. During this time, biomass, pH and pO2 were measured at 15 minute interval. The bacteria culture was induced after 4 hours of elapsed fermentation time (EFT4) with 1 mM IPTG and harvested after incubating for an additional 14 hours. Chemical lysis was performed on harvest samples and bacterial pellet samples were run on SDS-PAGE and analyzed using ImageJ densitometry software (see FIGS. 9A-D).

Based on the results obtained from the two-level fractional factorial design, three other high cell density (HCD) growth media were tested and further developed. They differ from each other with respect to their optimized response to either rhGDF5 expression (protein production) or biomass yield (growth rate) as follows: Media 1 (defined media improved rhGDF-5 expression) included sodium molybdate, magnesium sulfate and sodium chloride. Expression of rhGDF-5 was increased by increasing sodium molybdate, magnesium sulfate and sodium chloride in defined media (see Tables 6-7 and FIGS. 8A-B). Media 2 (semi-defined media improved rhGDF-5 expression) included magnesium sulfate and yeast extract. Expression of rhGDF-5 was increased in the presence of yeast extract and magnesium sulfate but decreased when sodium molybdate was present (see Tables 7-8 and FIGS. 9A-B). Media 3 (semi-defined media improved biomass yield) included yeast extract and tryptone while being negatively affected by sodium chloride and MOPS (see Tables 7-8 and FIGS. 9C-D).

As demonstrated in Table 7 and 8, Media 1 and 2 both enhanced the expression of rhGDF-5 while Media 3 improved or optimized biomass yield.

TABLE 7

| Media | Media Type | Optimized Response | Harvest $OD_{600}$ | rhGDF-5 Band Amount (μg/mL) |
|---|---|---|---|---|
| 1 | Defined | rhGDF-5 expression | 7.58 | 0.133 |
| 2 | Semi-Defined | rhGDF-5 expression | 8.3 | 1.03 |
| 3 | Semi-Defined | Biomass | 9.06 | 0.040 |
| 4 | Super Broth (Complex) | NA | 15.1 | 0.105 |

It was also noted that scale-up to 1 L volumes precipitated Media 2 while reduction in phosphates allowed the expression of rhGDF-5 and prevented precipitation of magnesium phosphate. Furthermore, substituting tryptone with peptone, a non-animal derived alternative, increased rhGDF-5 expression. Data not included herein.

Similar findings were obtained with a smaller scale fermentation (24-well plate) and the 2.5 L Ultra Yield Flask scale up fermentation methods with respect to the effect of Media 1 and 3 on GDF5 on biomass yield (see Table 8). Their effect on GDF-5 protein expression was not the same. Enhanced GDF5 protein expression was demonstrated when cultures were grown on the 24-well plate with Media 2 but not on Media 1 and Media 3. See data from Table 8. A problem was encountered with Media 2 during the 2.L-Ultra Yield Flask scale-up fermentation run. The solution precipitated during overnight storage which may have been due to magnesium sulfate reacting with phosphate-buffering system to form insoluble magnesium phosphates.

TABLE 8

| | | | | Media Alternatives | | | 2.5L UY Confirm. Run | | | 24 Well Plates | | |
|---|---|---|---|---|---|---|---|---|---|---|---|---|
| Media | Media Type | Optimized Response | ID | Harvest OD600 | rhGDF-5 band amount (μg) | rhGDF-5 amount per ml ferm (μg/ml) | Harvest OD600 | rhGDF-5 band amount (μg) | rhGDF-5 amount per ml ferm (μg/ml) | Harvest OD600 | rhGDF 5 band amount (μg) | rhGDF-5 amount per ml ferm (μg/ml) |
| 1 | Defined | rhGDF-5 expression | N/A | 8.64 | 0.6678 | 14.99 | 7.25 | 2.596 | 24.15 | 7.58 | 0.1402 | 1.023 |
| 2 | Semi defined | rhGDF-5 expression | 2a | 9.82 | 0.1913 | 6.278 | 7.79 | 0.4379 | 4.378 | 8.3 | 0.9934 | 7.936 |
| | | | 2b | 9.82 | 0.7756 | 16.37 | | | | | | |
| 3 | Semi defined | Biomass | 3 | 11.96 | 0.1406 | 10.11 | 12.2 | 3.343 | 52.34 | 9.06 | 0.0351 | 0.3060 |
| | | | 3a | 10.12 | 0 | 0 | | | | | | |
| | | | 3b | 10.42 | 0 | 0 | | | | | | |
| | | | 3c | 11.42 | 1.172 | 17.17 | | | | | | |
| 5B | Super Broth (Complex) | N/A | N/A | 22.72 | 1.609 | 46.92 | 19.06 | 2.181 | 53.34 | 15.1 | 0.1668 | 2.425 |

Effects of pH and Oxygen on the GDF-5 Protein Production and Expression

Figure 11C:
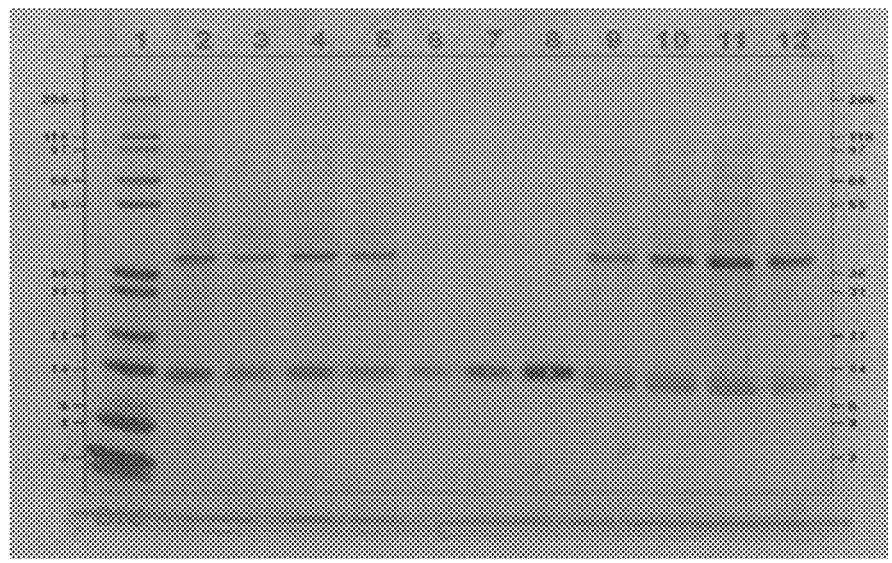

To study the effects of pH and oxygen on GDF-5 protein production and expression, pGDF5-Trc-transformed host cells (HMS174 strain, Clone F031512 were grown under the following growth conditions: (i) pH 6.5 (condition A); ii) pH 7.1 (condition B); and iii) pH 6.8 at low oxygen (condition C) and induced with IPTG. Samples designated hereinafter as F031512A, F031512AB, and F031512A C from each of the three conditions were normalized to 4.0 at $OD_{600}$ by dilution into BugBuster® Plus Lysonase™ (Novagen®) before separately running them under reducing and non-reducing SDS-PAGE conditions. Each of the sample pellets (EFT22, EFT24, EFT26 and EFT28 were resuspended in equal volume of water and added to 4× reducing sample buffer. All 3 SDS-PAGE gels (see FIGS. 11A-C), i.e., Samples F031512A, B, and C loaded on Gels A, B, and C, respectively, were stained and de-stained in the same gel tray. Intensity and banding pattern of the reference standards varied greatly from gel to gel. Densitometry data was generated comparatively. All calculations were based on standards value from the gel that produced a single band standard (Gel C). Though the overall yield estimations accuracy maybe questionable but their relative comparisons should be valid since the molecular weight ladder showed consistent band intensity at molecular weights similar to the protein of interest.

Figure 11D:
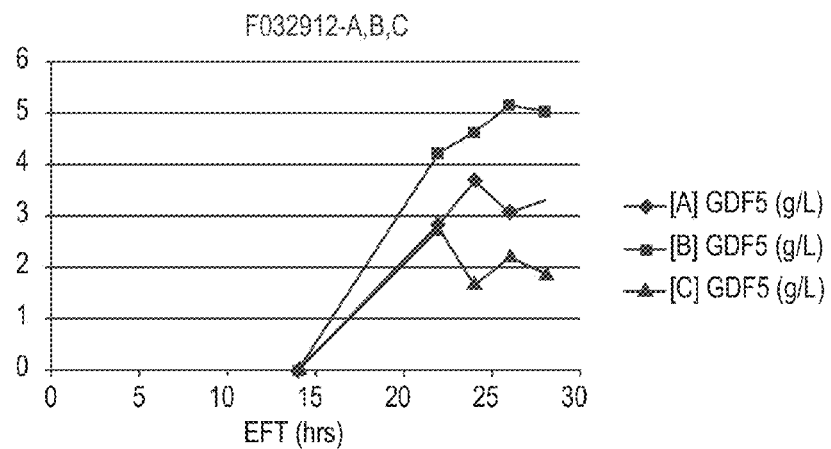
FIG. 11D shows the effect of pH and oxygen on protein expression and growth rate of pGDF5Trc-transformed HMS174 cells.
Figure 11E:
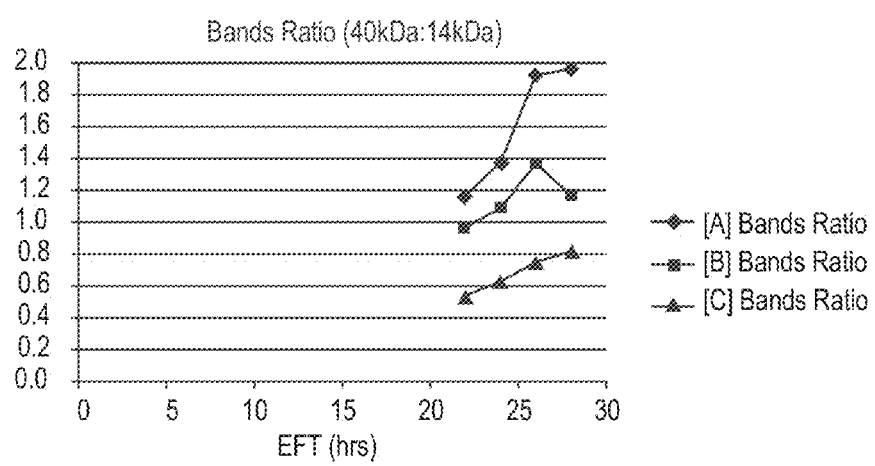
FIG. 11E shows the effect of pH and oxygen on the ratio of two major expressed bands, 40 kDa:14 kDa of pGDF5Trc-transformed HMS174 cells.

As shown in FIG. 11E, the F031512A samples resulted in a higher ratio of the two major expressed protein bands (40 kDa:14 kDa) than Samples F031512B and F031512C. Low oxygen (condition C) resulted in the lowest ratio of 40 kDa:14 kDa (FIG. 11E). Among the three conditions tested, cells that grew under growth media of pH 7.1 (condition B) had the highest overall GDF5 protein expression (FIG. 11B) and growth rate (see FIG. 11D) than cells that grew under condition A (growth media of pH 6.5; see FIG. 11A) and condition C (low oxygen condition; see FIG. 11C). Extreme reduction in dissolved oxygen leading to anaerobic conditions may not improve protein expression but can influence the ratio of 40 kDa:14 kDa (see FIGS. 11C and 11E).

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of isolating recombinant GDF-5 protein from an inclusion body of a prokaryotic cell, the method comprising: disrupting a prokaryotic host cell transformed with an expression vector having a T5 promoter operatively linked to a polynucleotide sequence that encodes a GDF-5 protein such that the prokaryotic host cell releases the inclusion body of GDF-5 protein and recovering the GDF-5 protein from the inclusion body by contacting the GDF-5 protein with a substrate, wherein the GDF-5 protein is a recombinant human GDF-5 (rhGDF-5) protein comprising the amino acid sequence of SEQ ID NO: 4.

2. The method of claim 1, wherein the disruption of the prokaryotic host cell is by lysing the cell or homogenization and the expression vector further comprises a kanamycin resistance (Kan') gene and a pUC origin of replication.

3. The method of claim 1, wherein the polynucleotide sequence is SEQ ID NO: 1 that encodes the polypeptide sequence of SEQ ID NO:4.

4. The method of claim 1, wherein the T5 promoter is inducible by isopropylthio-β-galactoside (IPTG).

5. The method of claim 1, wherein the expression vector is a plasmid vector that is pGDF5-T5.

6. The method of claim 5, wherein the pGDF5-T5 comprises the polynucleotide sequence of SEQ ID NO: 2.

7. The method of claim 1, wherein the prokaryotic host cell is an *Escherichia coli* cell comprises one of DH10β, STBL2, HMS174 or RecA.

8. The method of claim 1, wherein the prokaryotic cell disruption is performed via enzymatic cell disruption, sonication, dounce homogenization or high pressure release disruption.

9. The method of claim 1, wherein after prokaryotic cell disruption, the inclusion body is subjected to solubilization via denaturing agents and the denaturing agents comprise urea or guanidine hydrochloride.

10. A method of isolating recombinant GDF-5 protein from an inclusion body of a prokaryotic cell, the method comprising: providing a prokaryotic host cell comprising an expression vector comprising a T5 promoter operably linked to a polynucleotide sequence that encodes a GDF-5 protein, wherein the GDF-5 protein is a recombinant human GDF-5 (rhGDF-5) protein comprising the amino acid sequence of SEQ ID No: 4; disrupting the prokaryotic cell via lysis or homogenization such that the prokaryotic cell releases the inclusion body of rhGDF-5 protein; and recovering the GDF-5 protein from the inclusion body by contacting the rhGDF-5 protein with a substrate.

11. The method of claim 10, wherein the expression vector further comprises a kanamycin resistance (Kan$^r$) gene and a pUC origin of replication.

12. The method of claim 10, wherein the polynucleotide sequence is SEQ ID NO: 1 that encodes the polypeptide sequence of SEQ ID NO:4.

13. The method of claim 10, wherein the T5 promoter is inducible by isopropylthio-β-galactoside (IPTG) and wherein the expression vector is a plasmid vector that is pGDF5-T5.

14. The method of claim 13, wherein the pGDF5-T5 comprises the polynucleotide sequence of SEQ ID NO: 2.

15. The method of claim 10, wherein the prokaryotic host cell is an *Escherichia coli* cell comprises one of DH10β, STBL2, HMS174 or RecA.

16. The method of claim 10, wherein the prokaryotic cell disruption is performed via enzymatic cell disruption, sonication, dounce homogenization or high pressure release disruption.

17. The method of claim 10, wherein after prokaryotic cell disruption, the inclusion body is subjected to solubilization via denaturing agents and the denaturing agents comprise urea or guanidine hydrochloride.

* * * * *